United States Patent
Tan et al.

(10) Patent No.: US 10,307,296 B2
(45) Date of Patent: Jun. 4, 2019

(54) DEVICE FOR INSERTING AN IMPLANT AND METHOD OF USING THE SAME

(71) Applicant: National University of Singapore, Singapore (SG)

(72) Inventors: Kok Kiong Tan, Singapore (SG); Wenyu Liang, Singapore (SG); Phuong Pham Le, Singapore (SG); Sunan Huang, Singapore (SG); Hsueh Yee Lynne Lim, Singapore (SG); Chee Wee Gan, Singapore (SG)

(73) Assignee: National University of Singapore, Singapore (SG)

( * ) Notice: Subject to any disclaimer, the term of this patent is extended or adjusted under 35 U.S.C. 154(b) by 437 days.

(21) Appl. No.: 14/426,808

(22) PCT Filed: Sep. 10, 2013

(86) PCT No.: PCT/SG2013/000394
§ 371 (c)(1),
(2) Date: Mar. 9, 2015

(87) PCT Pub. No.: WO2014/042592
PCT Pub. Date: Mar. 20, 2014

(65) Prior Publication Data
US 2015/0238363 A1    Aug. 27, 2015

(30) Foreign Application Priority Data

Sep. 12, 2012  (SG) .............................. 201206799-7

(51) Int. Cl.
*A61F 11/00* (2006.01)
*A61B 17/34* (2006.01)

(52) U.S. Cl.
CPC ........ *A61F 11/002* (2013.01); *A61B 17/3468* (2013.01); *A61F 11/004* (2013.01)

(58) Field of Classification Search
CPC ........ A61F 2/002; A61F 2/004; A61F 11/002; A61F 11/004; A61B 17/32053; A61B 17/34; A61B 17/3468
See application file for complete search history.

(56) References Cited

U.S. PATENT DOCUMENTS

2007/0055291 A1    3/2007  Birkmeyer et al.
2007/0156164 A1*   7/2007  Cole ................ A61B 17/32053
                                                           606/187

(Continued)

FOREIGN PATENT DOCUMENTS

CN       202136476 U       2/2012
CN       102510746 A       6/2012

(Continued)

OTHER PUBLICATIONS

Written Opinion dated Oct. 5, 2015 from Singapore patent application No. 11201501528P.

(Continued)

*Primary Examiner* — Ryan J. Severson
*Assistant Examiner* — Christian D Knauss
(74) *Attorney, Agent, or Firm* — K. David Crockett, Esq.; Niky Economy Syrengelas, Esq.; Crockett & Crockett, PC

(57) ABSTRACT

In various embodiments, a device for inserting an implant on a human or animal body may be provided. The device may include an operable portion configured to make an incision on the human or animal body and configured to hold the implant for insertion on the human or animal body. The device may further include an actuator mechanism coupled to the operable portion, the actuator mechanism configured to move the operable portion along a first axis and configured to vibrate the operable portion along a second axis substantially perpendicular to the first axis.

14 Claims, 36 Drawing Sheets

(56) References Cited

U.S. PATENT DOCUMENTS

| | | | |
|---|---|---|---|
| 2007/0225787 A1* | 9/2007 | Simaan | A61N 1/0541 |
| | | | 607/137 |
| 2009/0209972 A1 | 8/2009 | Loushin et al. | |
| 2009/0299379 A1* | 12/2009 | Katz | A61F 11/002 |
| | | | 606/109 |
| 2010/0114288 A1* | 5/2010 | Haller | A61B 17/3468 |
| | | | 607/137 |
| 2012/0016192 A1* | 1/2012 | Jansen | A61B 1/005 |
| | | | 600/104 |
| 2012/0179187 A1 | 7/2012 | Loushin et al. | |

FOREIGN PATENT DOCUMENTS

| | | |
|---|---|---|
| GB | 2437708 A | 11/2007 |
| WO | WO2008131195 A2 | 10/2008 |
| WO | WO2009105619 A2 | 8/2009 |
| WO | WO2011008948 A1 | 1/2011 |
| WO | WO2012094666 A1 | 7/2012 |

OTHER PUBLICATIONS

Office Action dated Mar. 23, 2016 from Chinese Patent Application No. 201380059093.9.
European Search Report dated Mar. 30, 2016 from European Patent Application No. 13837612.4.
Office Action from European Patent Application No. 13837612.4 dated Nov. 27, 2018.

* cited by examiner

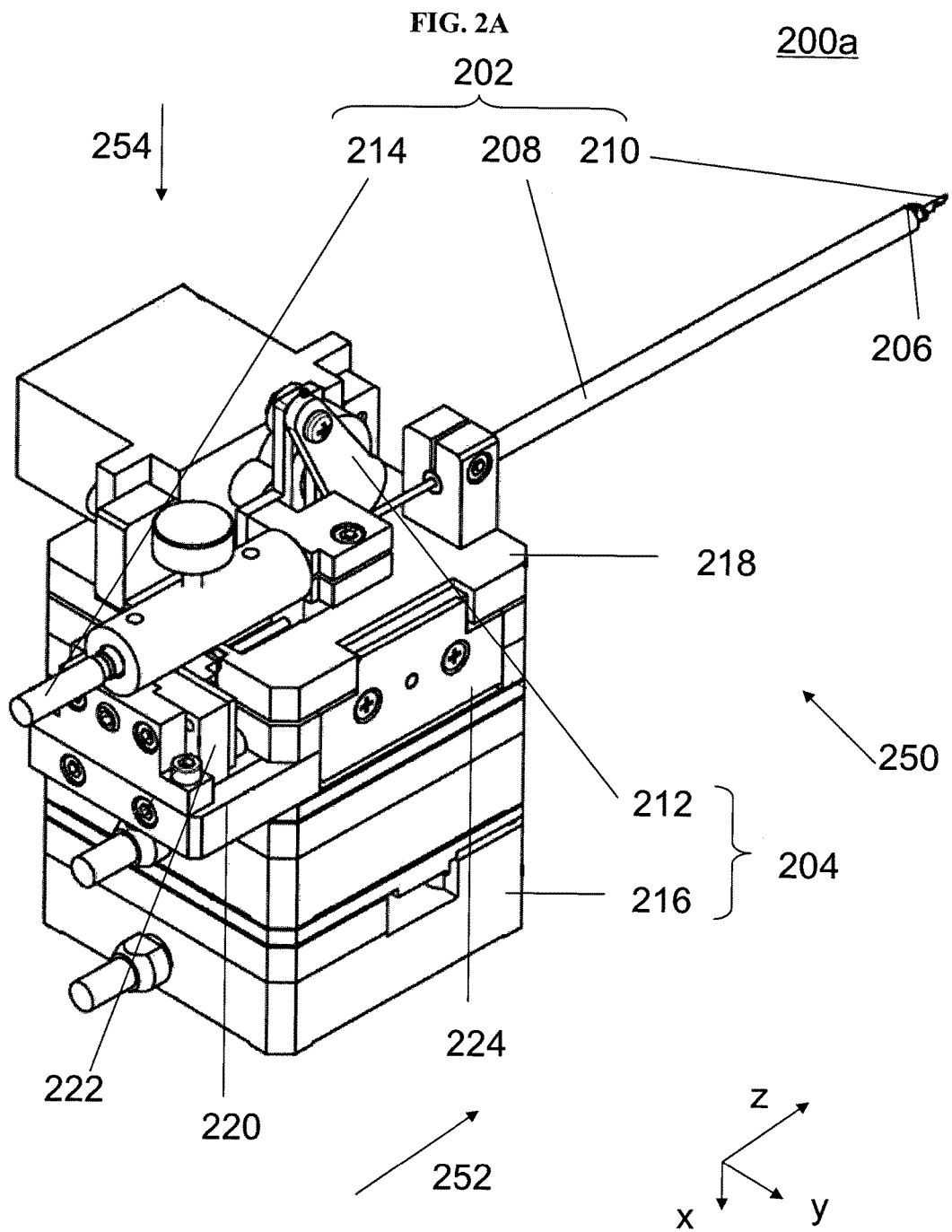

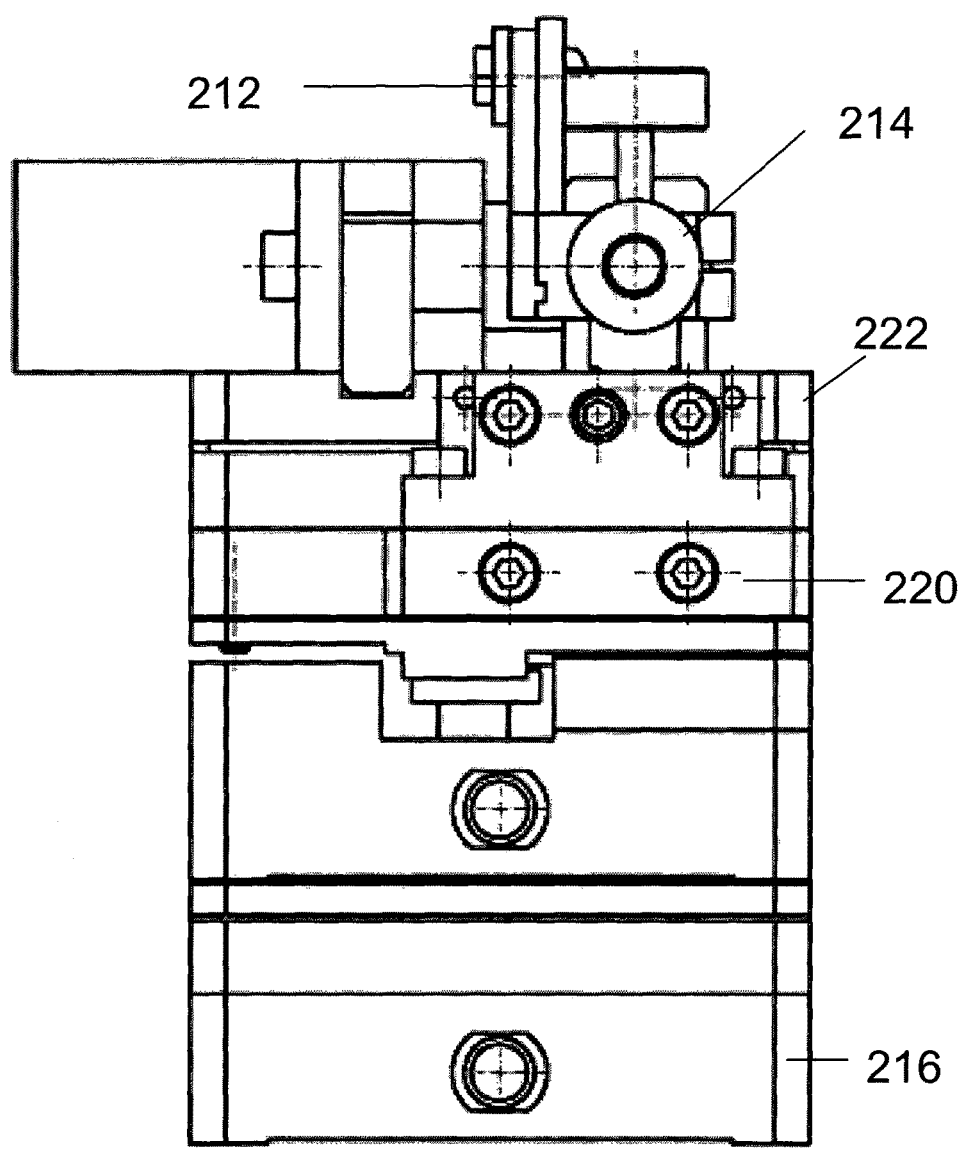

FIG. 11A

| | Frequency | Time |
|---|---|---|
| with vibration | 5Hz | 2.25s |
| | 10Hz | 0.9s |
| | 20Hz | 0.2s |
| | 30Hz | 0.1s |
| without vibration | Incision not achievable for 0.2mm Z-movement | |

1600 operating the device to move an operable portion of the device along a first axis and to move the operable portion of the device along a second axis perpendicular to the first axis to make an incision on the human or animal body

1602 using the device to insert the implant at least partially through the incision on the human or animal body

1604 ns; FIG. 10E is a side view showing the insertion of the

DEVICE FOR INSERTING AN IMPLANT AND METHOD OF USING THE SAME

CROSS-REFERENCE TO RELATED APPLICATIONS

This application claims the benefit of priority of SG application No. 201206799-7 filed Sep. 12, 2012, the contents of it being hereby incorporated by reference in their entirety for all purposes.

TECHNICAL FIELD

Various aspects of this disclosure relate to devices for inserting implants and methods of using the same.

BACKGROUND

Otitis media with effusion (OME) is a collection of fluid that occurs within the middle ear space due to the negative pressure caused by blockage of the Eustachian tube. This can occur purely from a viral upper respiratory tract infection or with acute bacterial otitis media. OME may cause hearing impairment. Over a period of time, the middle ear fluid can become very thick and glue-like, which increases the likelihood of the ear fluid causing conductive hearing impairment.

SUMMARY

In various embodiments, a device for inserting an implant on a human or animal body may be provided. The device may include an operable portion configured to make an incision on the human or animal body and configured to hold the implant for insertion on the human or animal body. The device may further include an actuator mechanism coupled to the operable portion. The actuator mechanism may be configured to move the operable portion along a first axis and configured to move or vibrate the operable portion along a second axis substantially perpendicular to the first axis.

In various embodiments, a method of using the device to insert an implant into a human or animal body. The method may include operating the device to move an operable portion of the device along a first axis and to move the operable portion of the device along a second axis perpendicular to the first axis to make an incision on the human or animal body. The method may further include using the device to insert the implant at least partially through the incision on the human or animal body.

In various embodiments, a device for use in a method of inserting an implant into a human or animal body may be provided. The method may include operating the device to move an operable portion of the device along a first axis and to move the operable portion of the device along a second axis perpendicular to the first axis to make an incision on the human or animal body. The method may further include using the device to insert the implant at least partially through the incision on the human or animal body.

BRIEF DESCRIPTION OF THE DRAWINGS

The invention will be better understood with reference to the detailed description when considered in conjunction with the non-limiting examples and the accompanying drawings, in which:

FIG. 2A shows a back right top perspective view of a device for inserting an implant on a human or animal body according to various embodiments. FIG. 2C shows a back view of the device in FIG. 2A according to various embodiments.

FIGS. 10A-J shows a method of using the device to insert an implant into a human or animal body according to various embodiments; wherein FIG. 10A is a side view of a operable portion of the device with an implant such as a grommet according to various embodiments; FIG. 10B is a side view showing the incision of the body part (e.g. myringotomy) using the cutting tool according to various embodiments; FIG. 10C is a side view showing the continued incision of the body part for insertion of the implant according to various embodiments; FIG. 10D is a side view showing the retraction of the cutting tool according to various embodiments; FIG. 10E is a side view showing the insertion of the implant as the operable portion is moved along the second axis according to various embodiments; FIG. 10F is a side view showing the continued insertion of the implant as the operable portion is moved along the first axis according to various embodiments; FIG. 10G is a side view showing the continued insertion of the implant as the operable portion is moved along the second axis in a direction opposite to the direction moved by the operable portion in FIG. 10E according to various embodiments; FIG. 10H is a side view showing the implant fully inserted in the incision according to various embodiments; FIG. 10I is a side view showing the continued insertion of the implant; and FIG. 10J is a side view showing the withdrawing of the operable portion after the implant is fully or at least partially inserted through the incision.

FIG. 11A is a table of the time taken to make the incision when vibrating the operable portion at different frequencies along the second axis according to various embodiments.

FIG. 16 is a schematic illustrating a method of using a device to insert an implant into a human or animal body

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

It should be understood that the terms "on", "top", "bottom", "down", "side", "back", "left", "right", "front" etc., when used in the following description are used for convenience and to aid understanding of relative positions or directions, and not intended to limit the orientation of any device or structures or any part of any device or structure.

Figure 1:
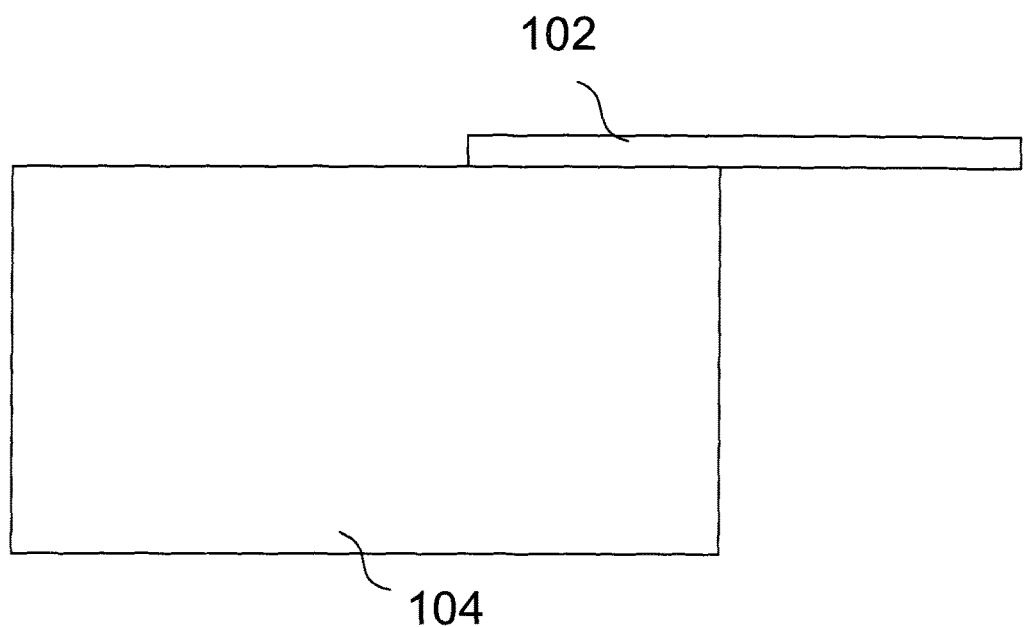
FIG. 1 shows, a right side view of a device for inserting an implant on a human or animal body according to various embodiments.

FIG. 1 shows a right side view 100 of a device for inserting an implant on a human or animal body according to various embodiments. The device may include an operable portion 102 configured to make an incision on the human or animal body and configured to hold the implant for insertion on the human or animal body. The device may further include an actuator mechanism 104 coupled to the operable portion 102. The actuator mechanism 104 may be configured to move the operable portion 102 along a first axis and configured to move or vibrate the operable portion 102 along a second axis substantially perpendicular to the first axis.

In other words, the device may be configured to insert an implant on a human or animal body. The device may include an operable portion 102. The operable portion 102 may be configured to make an incision on the human or animal body. The operable portion 102 may further be configured to hold the implant for insertion on the human or animal body. The device may also include an actuator mechanism 104. The actuator mechanism 104 may be configured to operate the operable portion 102. The actuator mechanism 104 may be configured to move the operable portion 102 along a first axis and may be further configured to move or vibrate the operable portion along a second axis which is perpendicular to the first axis.

In various embodiments, the device may be configured to treat ear infection such as OME. The implant may be a grommet or tube for draining fluid from the ear. The incision may be made on an ear membrane. The grommet or tube may then be inserted at least partially through the incision made on the ear membrane. Excess fluid may be drained out through the grommet or tube. The patient may be awake during the entire operation.

In various embodiments, the device may be a portable or hand-held device. Various embodiments allow for office-based grommet insertion. Various embodiments provide for simple, automated and quick "point, click and insert" operation to insert the grommet or tube. Various embodiments may remove or alleviate the administration of general anesthesia to the patient, costly expertise and equipment to perform the operation manually and/or reduce treatment delays. Various embodiments may allow the operator such as a surgeon to guide the device to the desired spot on the ear membrane. Various embodiments may further be configured to make an incision of the precise size on the membrane and to insert a grommet at least partially through or through the incision automatically, safely, speedily and/or with minimum trauma to the patient.

It may also be envisioned that the device may be used to insert other implants. For instance, the device may be configured to hold a microchip. The device may be configured to make an incision on the skin. The device may also be further configured to insert the microchip through the incision underneath the skin. It may also be envisioned that various systems, components or portions of the device may be used separately or for uses beyond grommet insertion.

The actuator mechanism 104 may be configured to move the operable portion 102 along the first axis and configured to move or vibrate the operable portion 102 along the second axis to make the incision. Additionally or alternatively, the actuator mechanism 104 may be configured to move the operable portion 102 along the first axis and configured to move or vibrate the operable portion 102 along the second axis to at least partially insert the implant.

In various embodiments, the operable portion 102 may include an elongated holder having a length extending from a first end of the holder to a second end of the holder. The elongated holder may be cylindrical in shape. The elongated holder may be configured to hold the implant at the first end of the holder. The elongated holder may further include a plurality of claws, such as two claws or three claws, to hold the implant at the first end of the holder.

The operable portion 102 may further include a cutting tool. The cutting tool may be configured to make the incision on the human or animal body. The cutting tool may include a two-step cutting edge. A two-step cutting edge allows the tip of the cutting tool to be sharper and still maintain the same length compared to a conventional surgery knife such as otology myringotomy blade. In various other embodiments, the cutting fool may include a multi-step cutting edge. The cutting tool may be configured to hold or engage the implant.

The elongated holder may include a cavity extending from the first end of the holder to the second end of the holder. The cavity of the elongated holder may be configured to receive the cutting tool.

In various embodiments, the cutting tool may include a hollow channel. The operable portion may further include a fiberscope or endoscope arranged at least partially within the hollow channel of the cutting tool. The fiber scope or endocope may include a lens at a first end of the fiber scope or endocope. The fiber scope or endocope may include a camera or an eye piece at a second end of the fiber scope or endocope. The fiberscope or endoscope may include a fiber line or fiber optics transmission line arranged along the hollow channel. The fiber line or fiber optics transmission line may couple the lens to the camera or the eye piece. The cutting tool may act as a hard shield for the fiberscope or endoscope. The cutting tool may further help to keep the view of the fiberscope or endoscope unblocked from impediment such as hair or other contaminants along the ear canal. It may also be envisioned that instead of a fiberscope or endoscope, the operable portion may include any other optical element or optical mechanism for capturing an image. The term "fiberscope" may refer to any optical element or optical mechanism for capturing an image.

In various embodiments, the operable portion 102 may include a telescopic design including the holder, the cutting tool and the fiberscope. In various embodiments, the length of the holder may be substantially parallel to the length of the cutting tool and the length of the fiberscope.

In various embodiments, the actuator mechanism 104 may further include a cutter retraction mechanism configured to move the cutting tool between a first position and a second position. The first position and the second position may be along a line substantially parallel to the length of the holder. The cutting tool may be received in the cavity of the elongated holder when the cutting tool is in the first position. The cutting tool may be protruded from the cavity of the elongated holder for making the incision on the human or animal body when the cutting tool is in the second position.

Additionally or alternatively, the cutting tool may be configured to move the cutting tool between the first position, the second position and an intermediate position between the first and second position.

The cutter retraction mechanism may include a servo motor. The servo motor may include a direct current (DC) motor. The servo motor may also include a gearbox as well as a potentiometer coupled to the DC motor.

The cutter retraction mechanism may further include a crank having a first end and a second end. The first end (of the crank) may be coupled to the servo motor. The second end (of the crank) may be coupled to the cutting tool. The second end (of the crank) may be coupled to the cutting tool via a rigid element such as a bar. The crank may be configured or positioned to convert the rotational motion of the servo motor to linear motion of the cutting tool between the first position and the second position (or between the first position, the second position and the intermediate position).

In various embodiments, the actuator mechanism 104 may include an actuator (such as a piezoelectric motor or piezoelectric actuator, e.g. an ultrasonic piezoelectric motor (USM)) to move the operable portion along the first axis. The actuator mechanism may further include a further actuator (such as a piezoelectric motor or piezoelectric actuator, e.g. an ultrasonic piezoelectric motor (USM)) to move or vibrate the operable potion along the second axis. The actuator and further actuator may provide a two degree of freedom (2-DOF) movement to the operable portion 102. In other words, the actuator mechanism 104 may include a 2-DOF stage including the actuator and the further actuator. An USM motor may provide a longer travelling range than other piezoelectric motors or piezoelectric actuators.

In various embodiments, the device may include a movable portion and a fixed portion. The operable portion 102 may be mounted on the movable portion. The movable portion and the operable portion 102 may be treated as a single rigid body. The force sensor may be coupled between the fixed portion and the movable portion. The force sensor may be configured to detect the force applied to the movable portion.

In various embodiments, the device may include the implant.

Figure 2B:
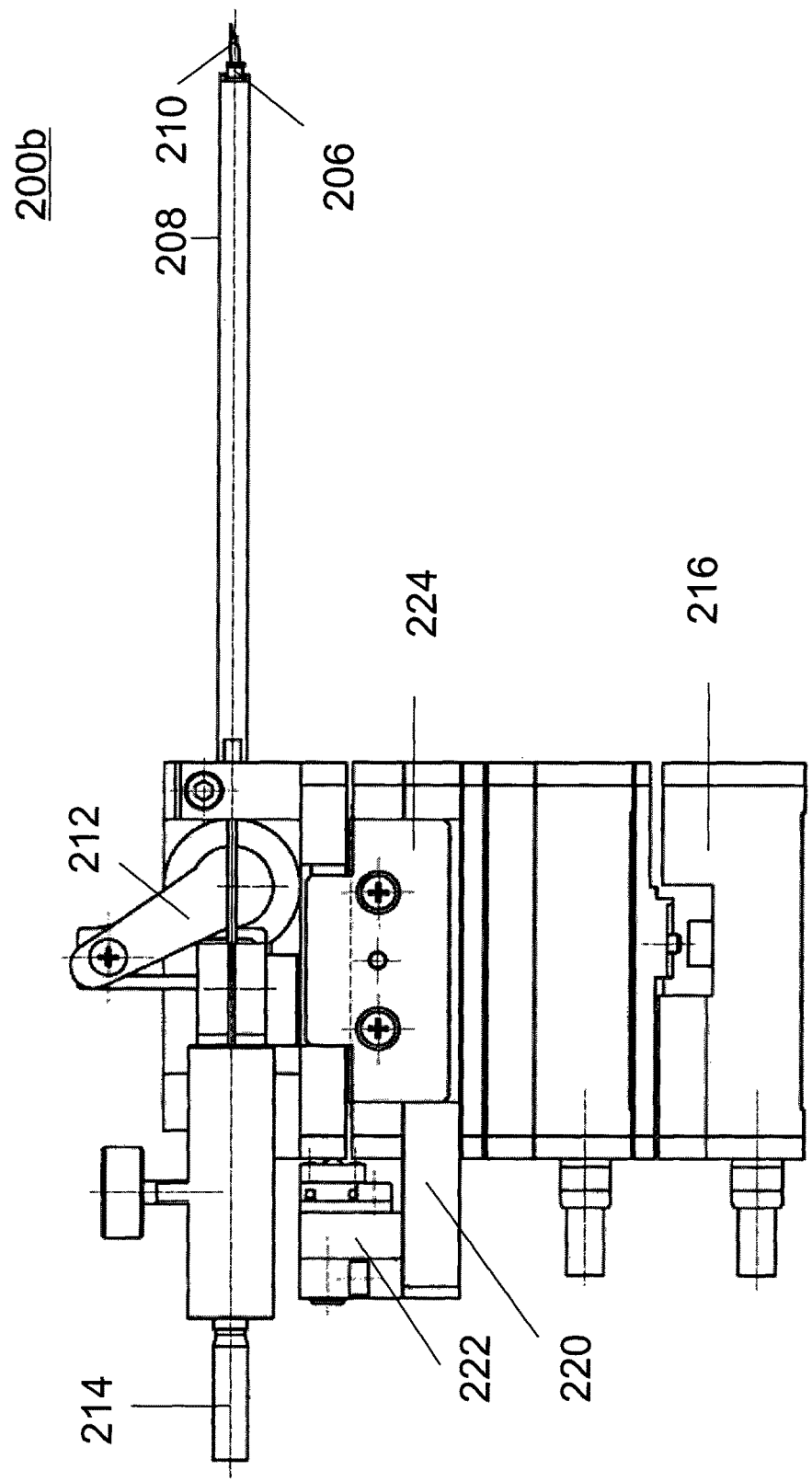
FIG. 2B shows a right side view of the device in FIG. 2A according to various embodiments.
Figure 2D:
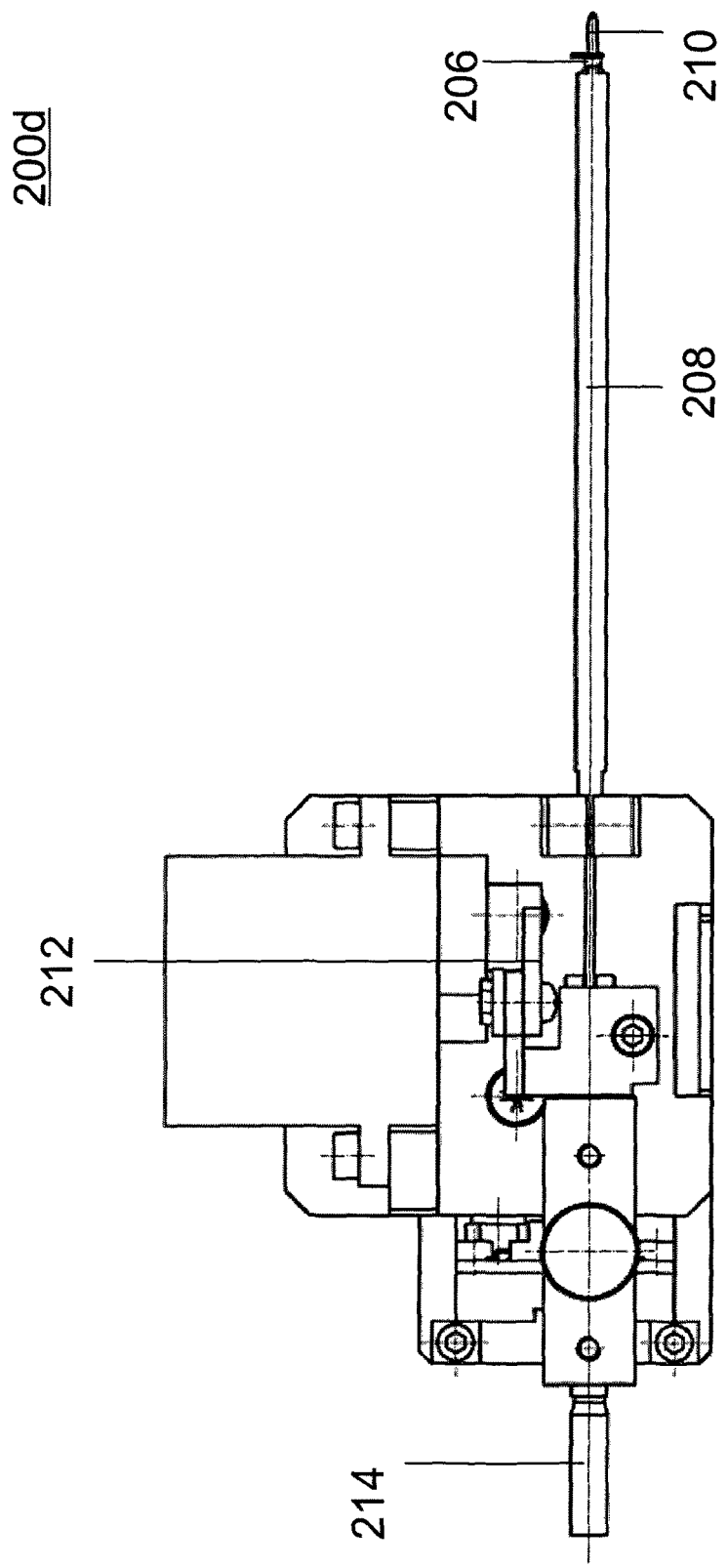
FIG. 2D shows a top view of the device in FIG. 2A according to various embodiments.

FIG. 2A shows a back right top perspective view 200a of a device for inserting an implant 206 on a human or animal body according to various embodiments. FIG. 2B shows a right side view 200b of the device in FIG. 2A according to various embodiments. FIG. 2B corresponds to the view when seen from the direction indicated by arrow 250 in FIG. 2A. FIG. 2C shows a back view 200c of the device in FIG. 2A according to various embodiments. FIG. 2C corresponds to the view when seen from the direction indicated by arrow 252 in FIG. 2A. FIG. 2D shows a top view 200d of the device in FIG. 2A according to various embodiments. FIG. 2C corresponds to the view when seen from the direction indicated by arrow 254 in FIG. 2A. The device may include an operable portion 202 configured to make an incision on the human or animal body and configured to hold the implant 206 for insertion on the human or animal body. The device may further include an actuator mechanism 204 coupled to the operable portion 202. The actuator mechanism 204 may be configured to move the operable portion 202 along a first axis and configured to move or vibrate the operable portion 202 along a second axis substantially perpendicular to the first axis.

The actuator mechanism 204 may be configured to move the operable portion 202 along the first axis and configured to move or vibrate the operable portion 202 along the second axis to make the incision. Additionally or alternatively, the actuator mechanism 204 may be configured to move the operable portion 202 along the first axis and configured to move or vibrate the operable portion 202 along the second axis to at least partially insert the implant.

In various embodiments, the operable portion 202 may include an elongated holder 208. The operable portion 202 may further include a cutting tool 210, the cutting tool 210 configured to make the incision on the human or animal body.

Figure 3A:
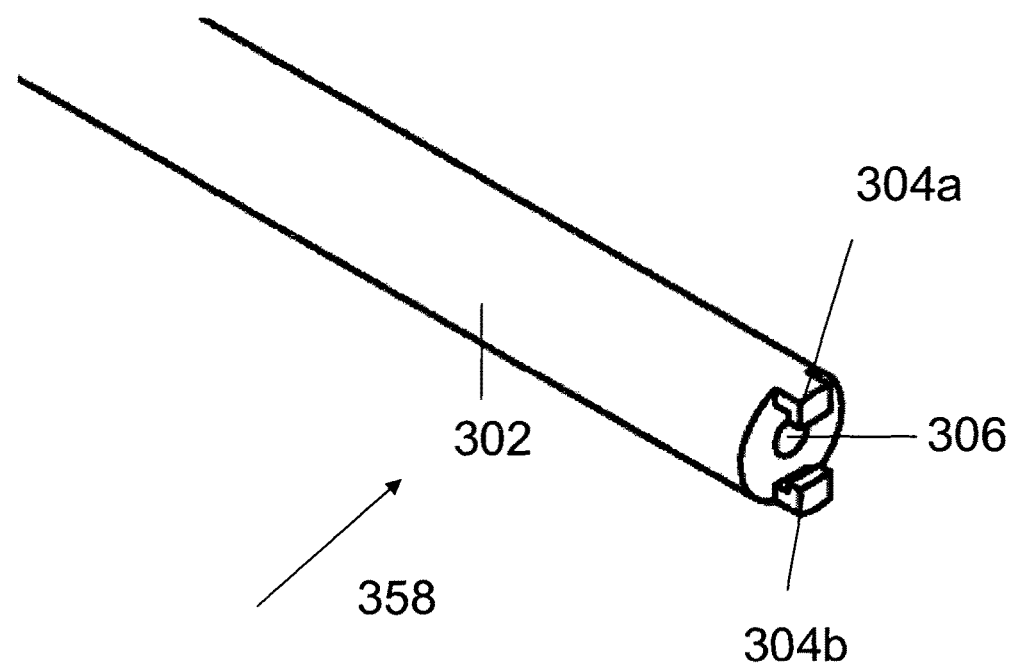
FIG. 3A shows a perspective view of an elongated holder according to various embodiments.
Figure 3B:
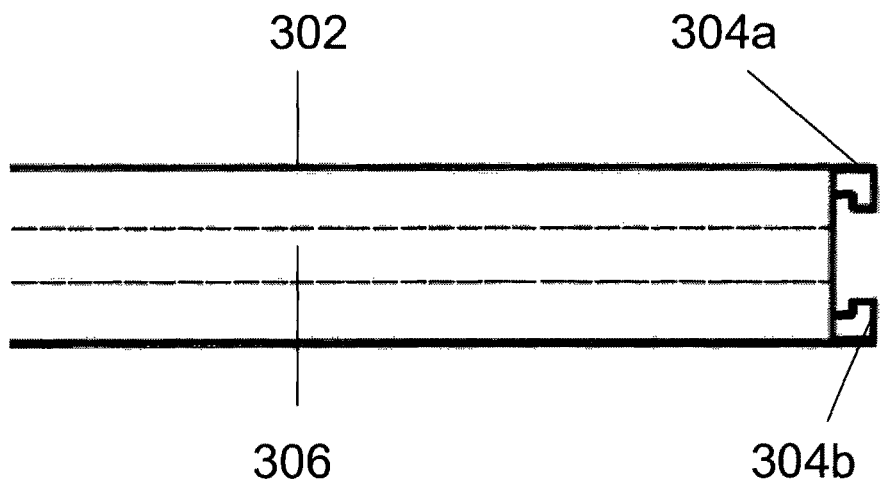
FIG. 3B shows a cross-sectional top view (indicated by the arrow in FIG. 3A) of the elongated holder in FIG. 3A according to various embodiments.

FIG. 3A shows a perspective view 300a of an elongated holder 302 according to various embodiments. FIG. 3B shows a cross-sectional top view (indicated by the arrow 358 in FIG. 3A) of the elongated holder 302 in FIG. 3A according to various embodiments. The elongated holder 302 may correspond to the elongated holder 208 in FIGS. 2A-D. The elongated holder 208, 302 may have a length extending from a first end of the holder to a second end of the holder. The elongated holder 208, 302 may be cylindrical in shape. The elongated holder 208, 302 may be configured to hold the implant at the first end of the holder 208,302. The elongated holder 208, 302 may further include two claws 304a, 304b, to hold the implant 206 at the first end of the holder 208, 302. The elongated holder 208, 302 may further include a cavity 306 extending from the first end of the holder to the second end of the holder 208, 302. The cavity 306 of the elongated holder 208, 302 may be configured to receive a cutting tool 210.

Figure 3C:
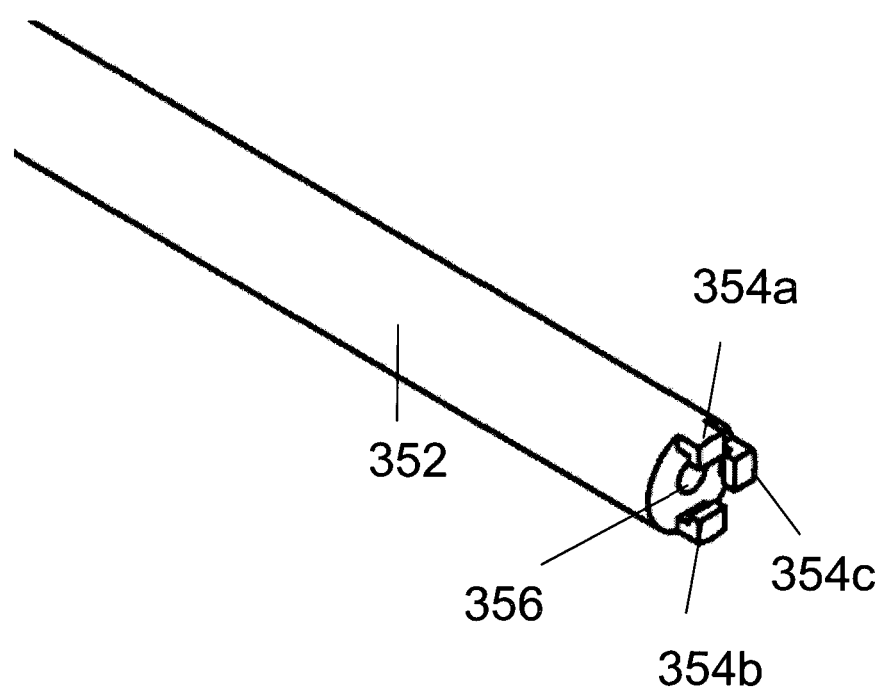
FIG. 3C shows a front right top perspective view of another elongated holder according to various embodiments

FIG. 3C shows a front right top perspective view 300c of another elongated holder 352 according to various embodiments. The elongated holder 352 may correspond to the elongated holder 208 in FIGS. 2A-D. The elongated holder 208, 352 may have a length extending from a first end of the holder to a second end of the holder. The elongated holder 208, 352 may be cylindrical in shape. The elongated holder 208, 352 may be configured to hold the implant at the first end of the holder 208, 352. The elongated holder 208, 352 may further include three claws 354a, 354b, 354c to hold the implant 206 at the first end of the holder 208, 352. The elongated holder 208, 352 may further include a cavity 356 extending from the first end of the holder to the second end of the holder 208, 352. The cavity 356 of the elongated holder 208, 356 may be configured to receive a cutting tool 210.

Figure 4A:
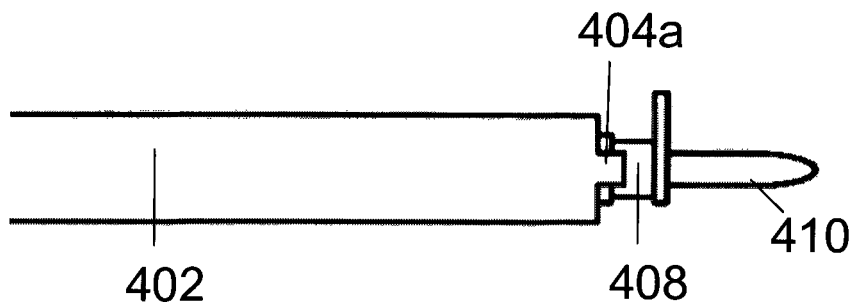
FIG. 4A shows a side view of the elongated holder holding an implant and with a cutting tool protruding from the holder according to various embodiments.
Figure 4B:
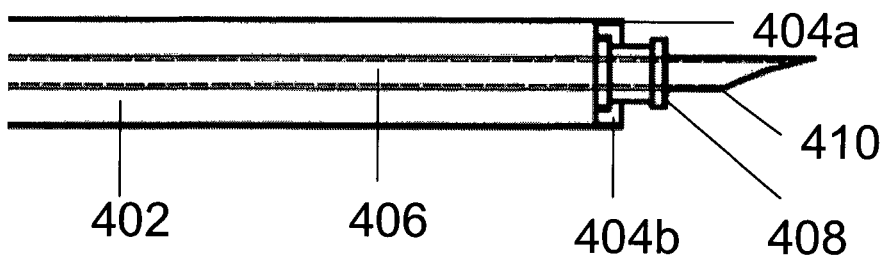
FIG. 4B shows a cross-sectional top view of the elongated holder holding the implant and with the cutting tool protruding from the holder as shown in FIG. 4A according to various embodiments.
Figure 4C:
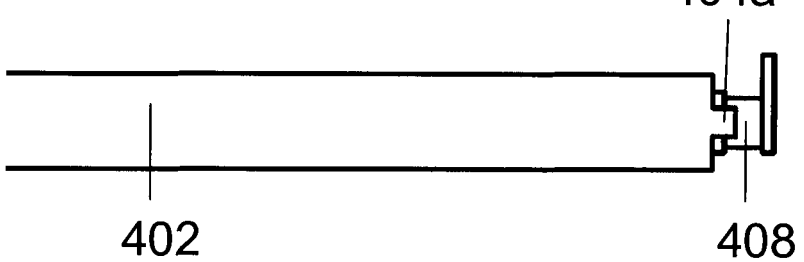
FIG. 4C shows a side view of the elongated holder holding an implant and with a cutting tool received in a cavity of the holder according to various embodiments.
Figure 4D:
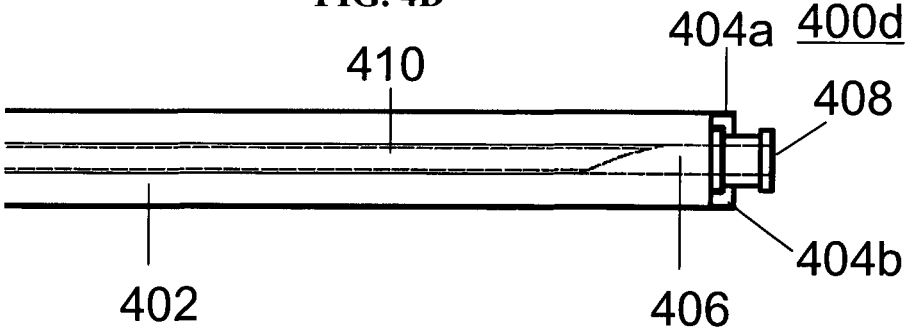
FIG. 4D shows a cross-sectional top view of the elongated holder holding the implant and with the cutting tool received in the cavity of the holder as shown in FIG. 4C according to various embodiments.

In various embodiments, the actuator mechanism 204 may further include a cutter retraction mechanism configured to move the cutting tool 210 between a first position and a second position. FIG. 4A shows a side view of the elongated holder 402 holding an implant 408 and with a cutting tool 410 protruding from the holder 402 according to various embodiments. FIG. 4B shows a cross-sectional top view of the elongated holder 402 holding the implant 408 and with the cutting tool 410 protruding from the holder as shown in FIG. 4A according to various embodiments. In FIG. 4A and FIG. 4B, the cutting tool 410 is in the second position. FIG. 4C shows a side view of the elongated holder 402 holding an implant 408 and with a cutting tool 410 received in a cavity 406 of the holder 402 according to various embodiments. FIG. 4D shows a cross-sectional top view of the elongated holder 402 holding the implant 408 and with the cutting tool 410 received in the cavity 406 of the holder 402 as shown in FIG. 4C according to various embodiments. In FIG. 4A and FIG. 4B, the cutting tool 410 is in the first position. The holder 402 in FIGS. 4A-E may correspond to the holder 208 in FIGS. 2A-D. The cutting tool 410 in FIGS. 4A-E may correspond to the cutting tool 210 in FIGS. 2A-D. The implant 408 in FIGS. 4A-E may correspond to the implant 206 in FIGS. 2A-D. The first position and the second position may be along a line substantially parallel to the length of the holder 208, 402. The cutting tool 210, 410 may be received in the cavity of the elongated holder 402, 208 when the cutting tool 210, 410 is in the first position. The cutting tool 410 may be protruded from the cavity 406 of the elongated holder 208, 402 for making the incision on the human or animal body when the cutting tool 210, 410 is in the second position.

In various embodiments, the actuator mechanism 204 may be configured to move the operable portion along the first axis and may be configured to move or vibrate the operable portion 202 along a second axis substantially perpendicular to the first axis to make the incision. The actuator mechanism 204 may be configured to move the operable portion along the first axis and to move or vibrate the operable portion 202 along the second axis simultaneously to make the incision. In various embodiments, the actuator mechanism 204 may be configured to move the operable portion along the first axis and may be configured to move the operable along the first axis to insert the implant through or at least partially through the incision. In various embodiments, the actuator mechanism 204 may be configured to move the operable portion along the first axis and may be configured to move the operable along the first axis to insert the implant on the human or animal body 210. In other words, the operable portion 202 maybe configured to weave the implant 206, 408 into place on the human or animal body 210.

Figure 4E:
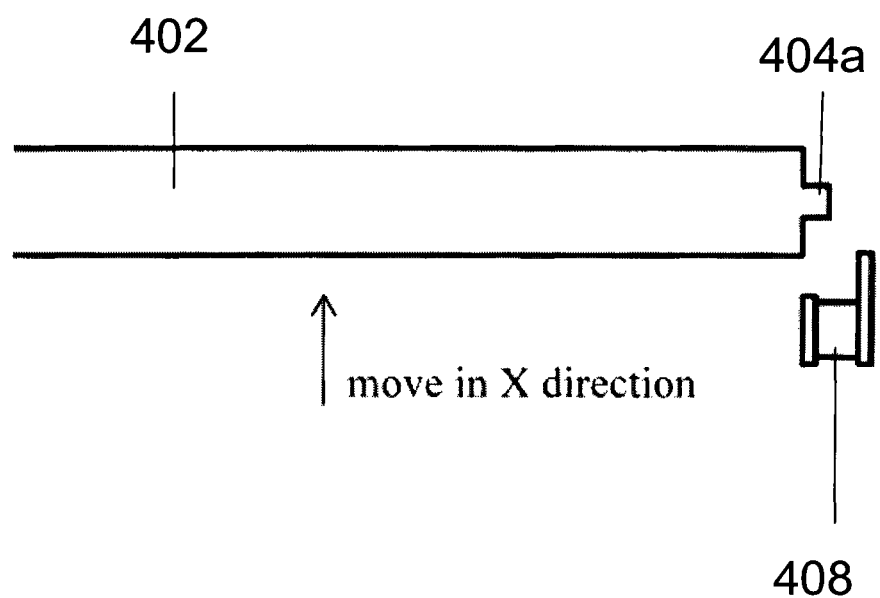
FIG. 4E is a side view showing the holder moving along the second axis (x axis) to release or disengage the implant.

The elongated holder 208 may be configured to hold the implant 206 as the elongated holder 208 moves along the first axis (e.g. z axis). The elongated holder 208 may be configured to release the implant 206 (and on the human or animal body) when the elongated holder moves along the second axis (e.g. x axis). In other words, the plurality of claws on the first end of the holder 208, 402 may be configured such that the plurality of claws (e.g. 404a, 404b) holds on to the implant 206, 408 when the operable portion 202 moves along the first axis. The implant 206, 408 may be prevented from being moved constrained in the axial direction (i.e. along the first axis (x-axis)) by the claws (e.g. 404a, 404b) and/or holder 208, 402. The implant 206, 408 may be constrained in the radial direction (i.e. y-axis and x-axis) by the cutting tool 210, 410 and/or the claws. For the holder 352 shown in FIG. 3C, the claw 354c may prevent the implant from moving in one direction along the second axis (i.e. x axis). The actuation mechanism 204 may be configured to retract the cutting tool 210 at least partially into the cavity of the holder 208, 402 after incision. Upon retraction, the actuation mechanism 204 may be configured to move along the second axis (x axis) to release the implant as the implant 206, 408 is no longer constrained along the second axis (x axis). FIG. 4E is a side view showing the holder 208, 402 moving along the second axis (x axis) to release or disengage the implant 206, 408. For the holder 352 shown in FIG. 3C, the third claw 354c may constrain the implant 206 in a first direction along the second axis. The actuation mechanism 204 may be configured to move the holder 352 such that the implant is released in a second direction along the second axis opposing the first direction.

In various embodiments, the implant 206 may be a grommet. The grommet may be configured to be implanted on to the ear membrane for treatment of ear infection such as OME. The grommet may be a tubular structure with a through hole running from a first end of the tubular structure to a second end of the tubular structure. The grommet may have an inner diameter extending across the diameter of the through hole. The grommet may have an outer diameter extending along a straight line from a first point along the circumference of the grommet across a central point of the grommet to a second point along the circumference of the grommet. The elongated holder 208 may have an inner diameter extending across the diameter of the cavity on one end of the elongated holder 208. The elongated holder 208 may have an outer diameter extending along a straight line from a first point along the circumference of the elongated holder 208 across a central point of the elongated holder 208 to a second point along the circumference of the elongated holder 208 on one end of the elongated holder. The elongated holder 208 may have an uniform outer diameter and an uniform inner diameter through the length of the elongated holder 208. In various embodiments, the outer diameter of the elongated holder 208 may be less or equal to half the diameter of an average ear canal. The inner diameter may be substantially equal to the inner diameter of the grommet. The length of the elongated holder 208 may be about 1.5 times the length of an average ear canal.

Figure 5A:
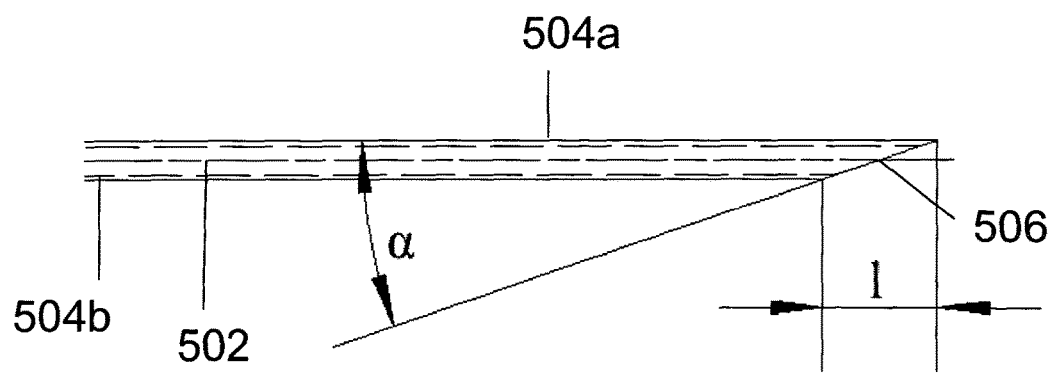
FIG. 5A shows a side view of a cutting tool according to various embodiments.
Figure 5B:
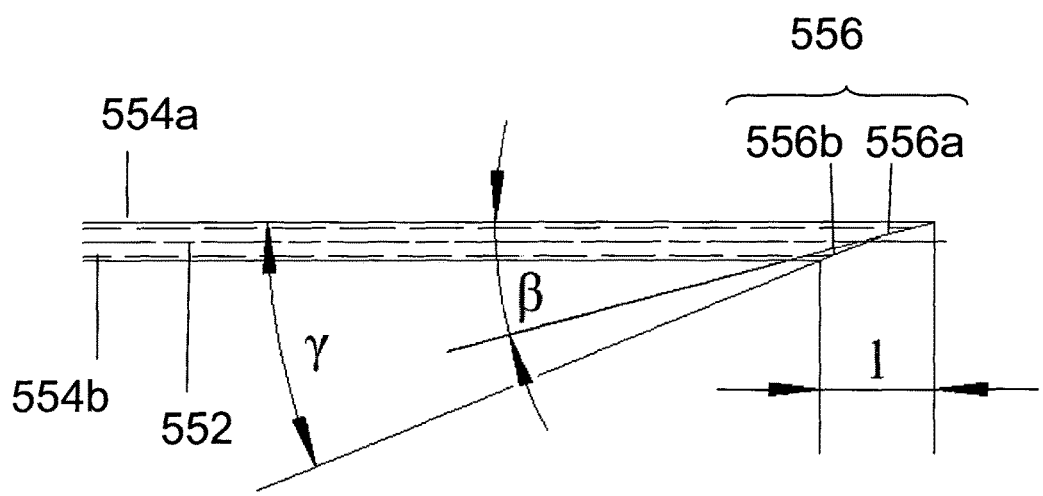
FIG. 5B shows a side view of a cutting tool according to various embodiments.

FIG. 5A shows a side view 500a of a cutting tool 502 according to various embodiments. The cutting tool 502 may include a first cutting edge 504a and a second cutting edge 504b substantially parallel to the first cutting edge 504a. The first cutting edge 504a may be longer than the second cutting edge 504b. The first cutting edge 504a may be longer than the second cutting edge 504b by a length 1. The cutting tool 502 may further include a third cutting edge 506 joining the first cutting edge 504a and the second cutting edge 504b. The third cutting edge 506 may join the first cutting edge 504 at an angle α. The third cutting edge 506 may be a single step cutting edge. In other words, the third cutting edge 506 may be a straight line joining the first cutting edge 504a and the second cutting edge 504b. FIG. 5B shows a side view 500b of a cutting tool 552 according to various embodiments. The cutting tool may include a first cutting edge 554a and a second cutting edge 554b substantially parallel to the first cutting edge 554a. The first cutting edge 554a may be longer than the second cutting edge 554b. The first cutting edge 554a may be longer than the second cutting edge 554b by a length 1. The cutting tool 552 may further include a third cutting edge 556 joining the first cutting edge 554a and the second cutting edge 554b. The third cutting edge 556 may include a first step (or portion) 556a and a second step (or portion) 556b. In other words, the cutting tool may include a two-step cutting edge 556. The first step (or portion) 556a may make an angle β with the first cutting edge 554a. The second step (or portion) 556b may make an angle γ with the first cutting edge 554a. The first step (or portion) 556a may form a tip with the first cutting edge 554a. The angle β may be smaller than the angle γ. Having a two-step cutting edge allows for a sharper tip (as the first step 556a makes a smaller angle with the first cutting edge 554a) while maintaining the same length 1 as the cutting tool shown in FIG. 5A. The cutting tool 502, 552 may be a needle or surgical cutter. A cutting tool having a multi-steps or multi-portion cutting edge may also be envisioned.

The actuation mechanism 204 may be configured to retract the cutting tool 210 into the cavity of the holder 208 after incision by a cutter retraction mechanism 212. In various embodiments, the actuation mechanism 204 may include a cutter retraction mechanism 212. The cutter retraction mechanism 212 may be configured to move the cutting tool 210 between a first position and a second position. The cutting tool 210 may be received in the cavity of the elongated holder 208 when the cutting tool is in the first position. The cutting tool 210 may be protruded from the cavity of the elongated holder 208 for making the incision on the human or animal body when the cutting tool 210 is in the second position. The cutter retraction mechanism 212 may instead be configured to move the cutting tool 210 between the first position, the second position and an intermediate position between the first position and the second position. When the cutting tool 210 is in the first position and/or in the intermediate position, the implant 206 may no longer be in engagement with the cutting tool 210. As the implant 206 is no longer being held by the cutting tool 210, the implant 206 may be disengaged or released by the operable portion 202 for insertion into the human or animal body. The cutter retraction mechanism 212 may retract the cutting tool 210 to the first position or the intermediate position and so releases or disengages the implant 206 from the operable portion 202.

Figure 6A:
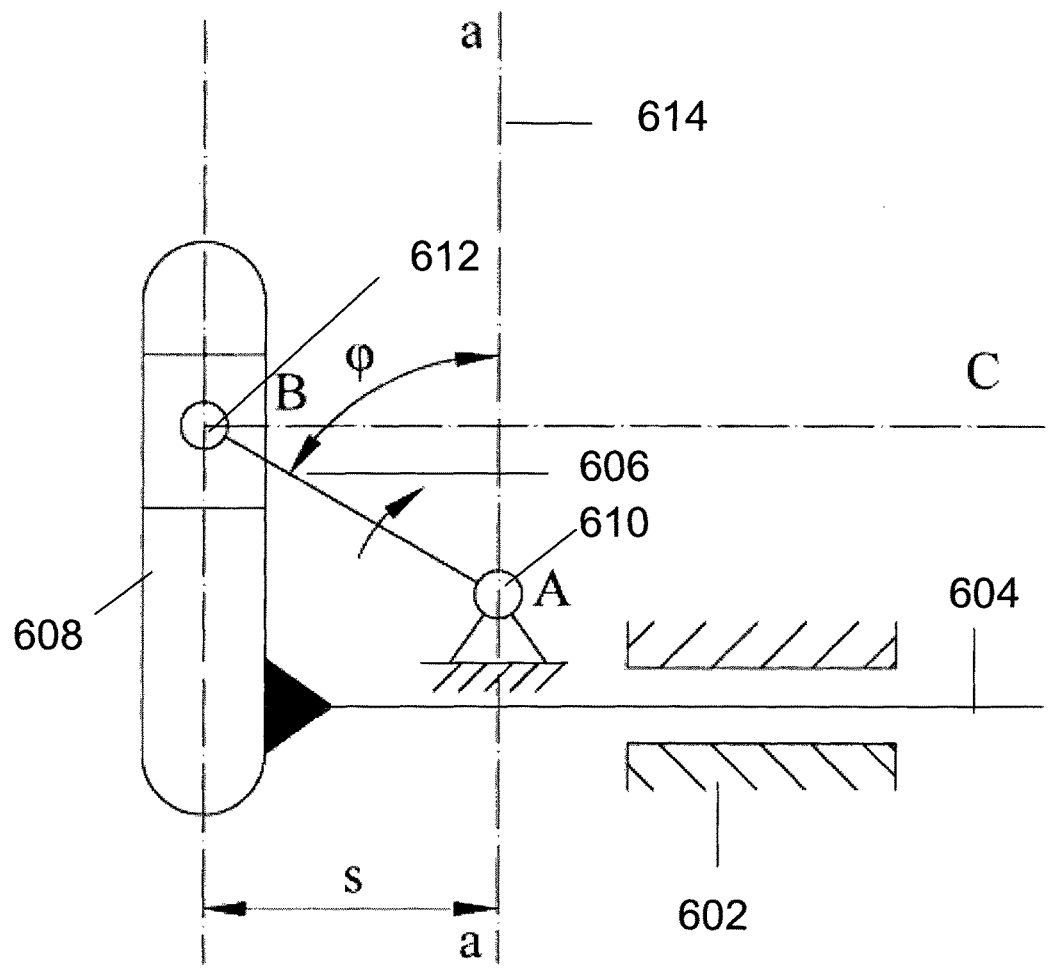
FIG. 6A is a schematic of a retraction mechanism according to various embodiments.
Figure 6B:
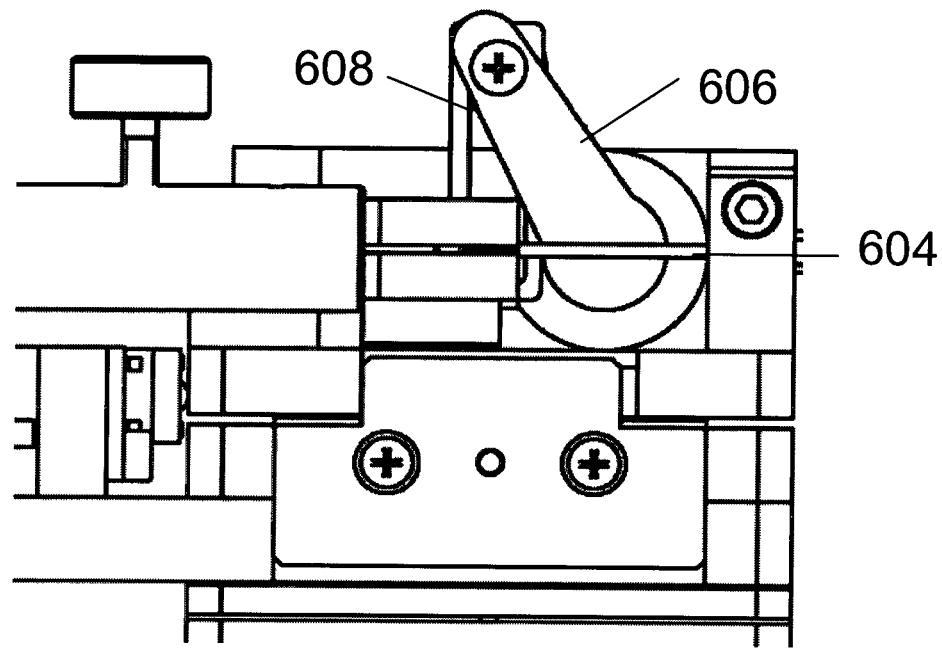
FIG. 6B shows the right side view of a portion of the retraction mechanism according to various embodiments when the cutting tool is in the second position.
Figure 6C:
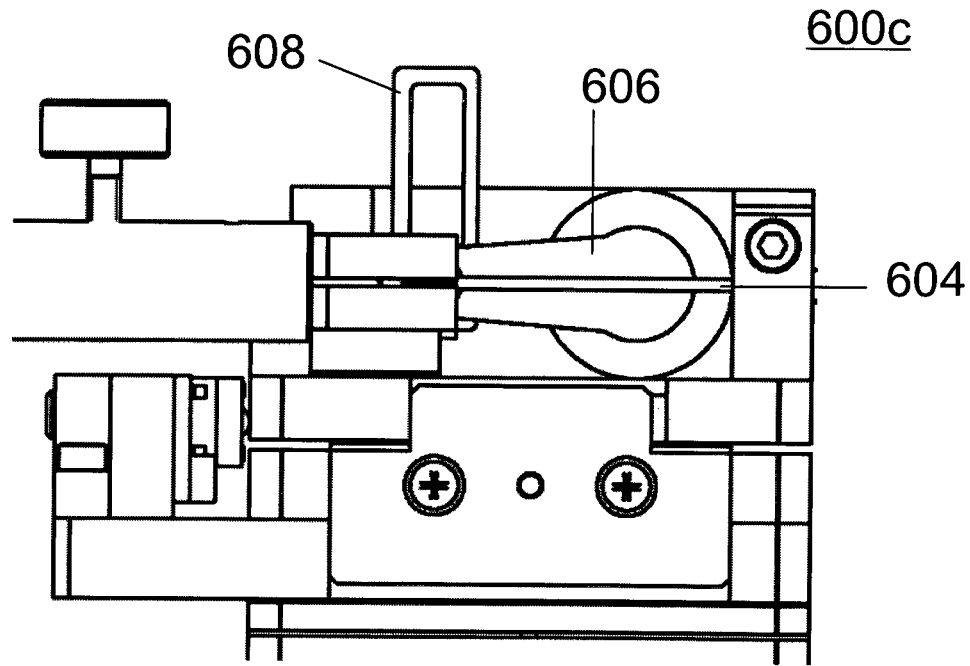
FIG. 6C shows the right side view of a portion of the retraction mechanism according to various embodiments when the cutting tool is in the first position.

FIG. 6A shows a schematic 600a of a retraction mechanism according to various embodiments. The retraction mechanism may be a sine generator mechanism. FIG. 6B shows the right side view of a portion of the retraction mechanism according to various embodiments when the cutting tool 604 is in the second position. FIG. 6C shows the right side view of a portion of the retraction mechanism according to various embodiments when the cutting tool 604 is in the first position. The cutting tool 604 in FIGS. 6A-C may correspond to the cutting tool 210 in FIGS. 2A-D. The cutter retraction mechanism in FIGS. 6A-C may also correspond to the cutter retraction mechanism 212 in FIGS. 2A-D. In various embodiments, the cutter retraction mechanism 212 may include a servo motor. The cutter retraction mechanism 212 may further include a crank 606 having a first end and a second end. The first end (of the crank 606) may be coupled to the servo motor. The second end (of the crank 606) may be coupled to the cutting tool 210, 604. In various embodiments, the second end (of the crank 606) may be coupled to the cutting tool 210, 604 via a bar 608. The cutting tool 210, 604 may be coupled to the bar 608 via a first pivot 612. The cutting tool 210, 604 may be attached or fixed to the bar 608.

The crank 606 may be configured to convert rotational motion of the servo motor to linear motion of the cutting tool 210, 604 between the first position and the second position. The servo motor may rotate the crank 606 about a second pivot 610. As the crank rotates about the second pivot 610, the bar 608 may move. The bar 608 may move in a linear manner, i.e. the bar 608 may move from a first position to a second position such that the length of the bar 608 when the bar 608 is in the first position is parallel to the length of the bar 608 when the bar 608 is in the second position. In various embodiments, the bar 608 may rotate (clockwise or anti-clockwise) about the first pivot 612. In various embodiments, the first pivot 612 may also slide along the length of the bar 608. In various embodiments, the pivoting motion of the crank 606 about the first pivot 612 and/or the sliding motion of the first pivot 612 along the length of the bar 608 may cause the cutting tool 210, 604 (which may be fixed rigidly to the bar 608) to move linearly along guide 602. The guide 602 may be the holder 208. The stroke, s, of the sine generator mechanism may be provided by the following equation:

$$S = L \sin\phi \quad (1)$$

where L is the length of crank 606 and $\phi$ is the angle the crank 606 makes with axis 614.

As the crank $\phi$ changes from 30° (as shown in FIG. 6B) to 90° (as shown in FIG. 6C), the cutting tool 210, 604 may be retracted into the cavity of the holder 208. The stroke, s, may vary from 0.5 L (when ϕ is 30°) to L (when ϕ is 90°). As such, the change in stroke is 0.5 L. The change in stroke may be referred to as the cutter retraction stroke. As advantageously, the sine generator mechanism (in which the stroke varies as a sine function of angle ϕ) may allow for actual linear displacement of the cutting tool 210, 604 to be determined easily via the sine rotational angle ϕ. The crank 606 may act as a low cost rotary-linear coupler and provides a simple sine relationship between the rotation angle and linear displacement of the cutting tool 210, 604. In addition, the link mechanism (e.g. the crank 606 and the bar 608) may be easy to fabricate. Further the undesirable backlash which may affect the precision of the device may be minimized compared to other coupling mechanism such as using lead screw.

Figure 7A:
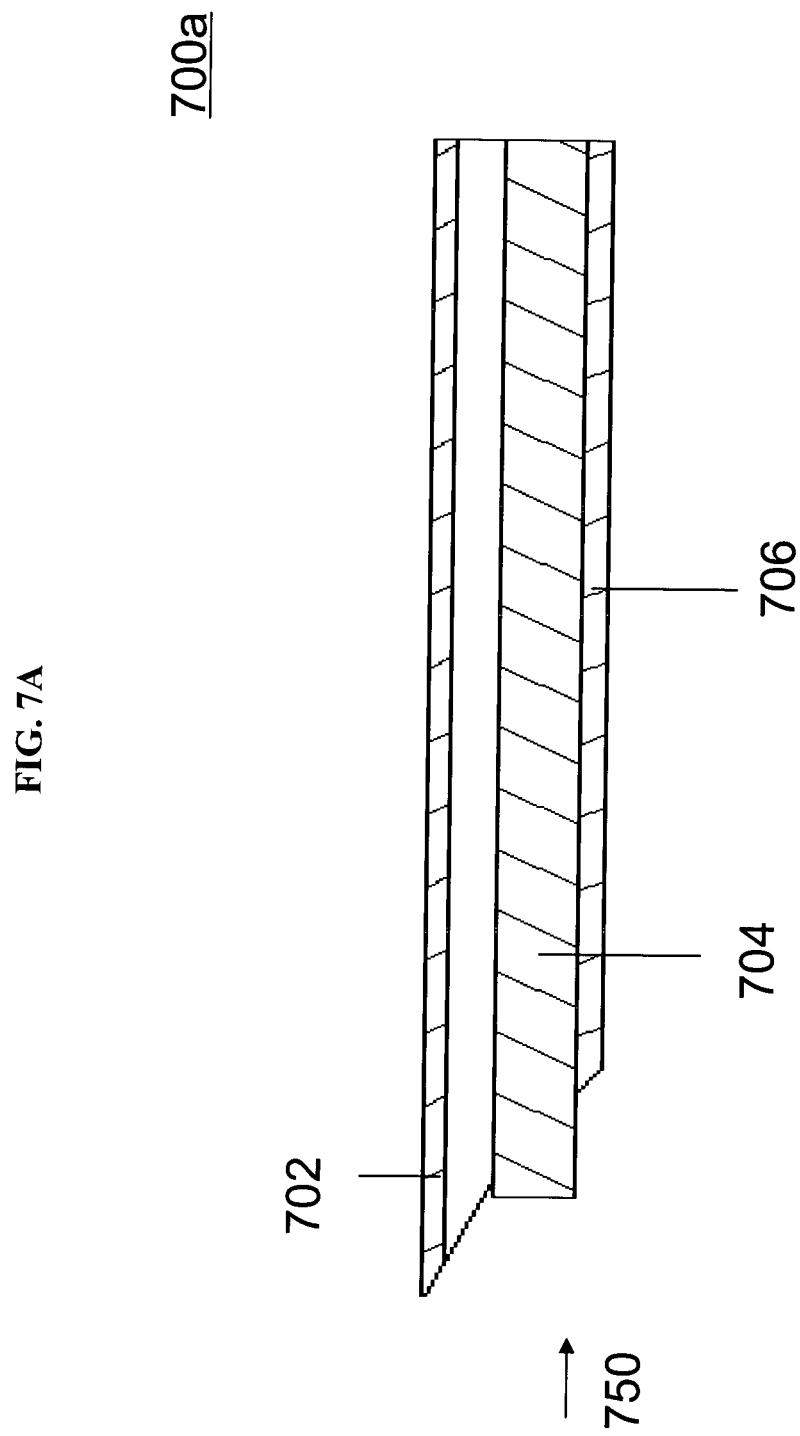
FIG. 7A shows a left cross-sectional view of a cutting tool according to various embodiments.

FIG. 7A shows a left cross-sectional view 700a of a cutting tool according to various embodiments. The cutting tool 702 in FIG. 7A may correspond to the cutting tool 210 in FIGS. 2A-D. The endoscope or fiberscope 704 in FIG. 7A may correspond to the endoscope or fiberscope 214 in FIGS. 2A-D. In various embodiments, the cutting tool 210, 702 may further include a hollow channel 706. The operable portion 202 may further include a fiberscope or endoscope 214, 704 (e.g. ear endoscope) arranged at least partially within the hollow channel 706 of the cutting tool 210, 702. The fiberscope or endoscope 214, 704 may include a lens (not shown) at a first end of the fiberscope or endoscope 214, 704. The first end of the fiberscope or endoscope 214, 704 may be the end of the fiberscope or endoscope 210, 70 nearer the tip of the cutting tool 214, 704. The fiberscope or endoscope 214, 704 may include a camera or an eye piece (not shown) at a second end of the fiber scope or endoscope 214, 704. The fiberscope or endoscope 214, 704 may include a fiber line or fiber optics transmission line arranged along the hollow channel 706. The fiber line or fiber optics transmission line may couple the lens to the camera or the eye piece. The cutting tool 214, 704 may act as a hard shield for the fiberscope or endoscope. The cutting tool may further help to keep the view of the fiberscope or endoscope 214, 704 unblocked from impediment such as hair or other contaminants along the ear canal. In order to reduce the weight of the device, parts of the imaging system coupled to the endoscope or fiberscope 214, 704 may be housed outside the device. For instance, an optics fiber or an electrical signal transmission line may transmit an optical or electrical signal from the device to a display.

Figure 7B:
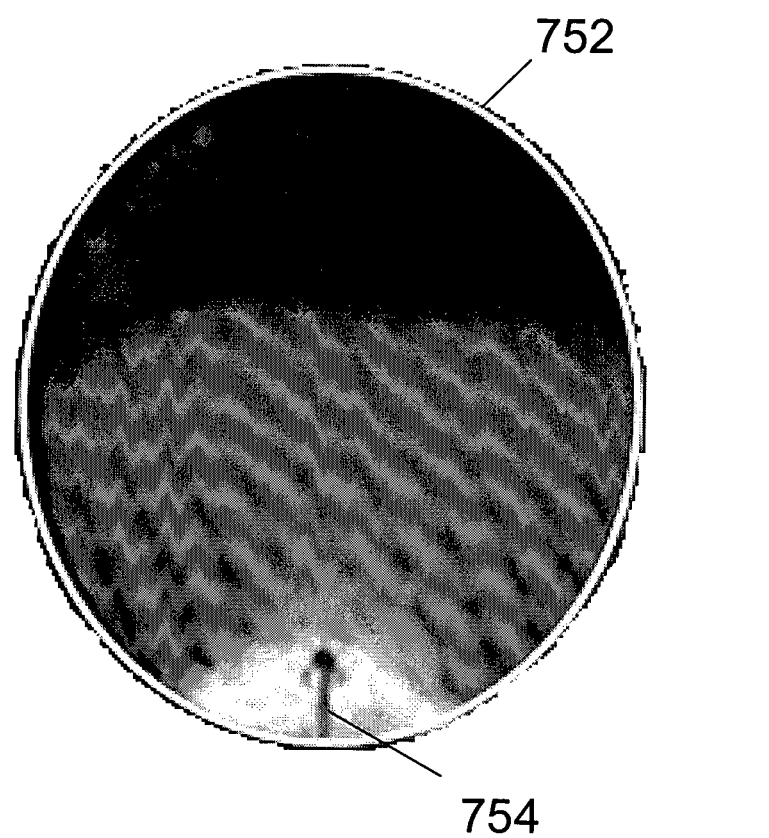
FIG. 7B is a photo seen by the fiberscope when the device according, to various embodiments, is placed in a room environment.
Figure 7C:
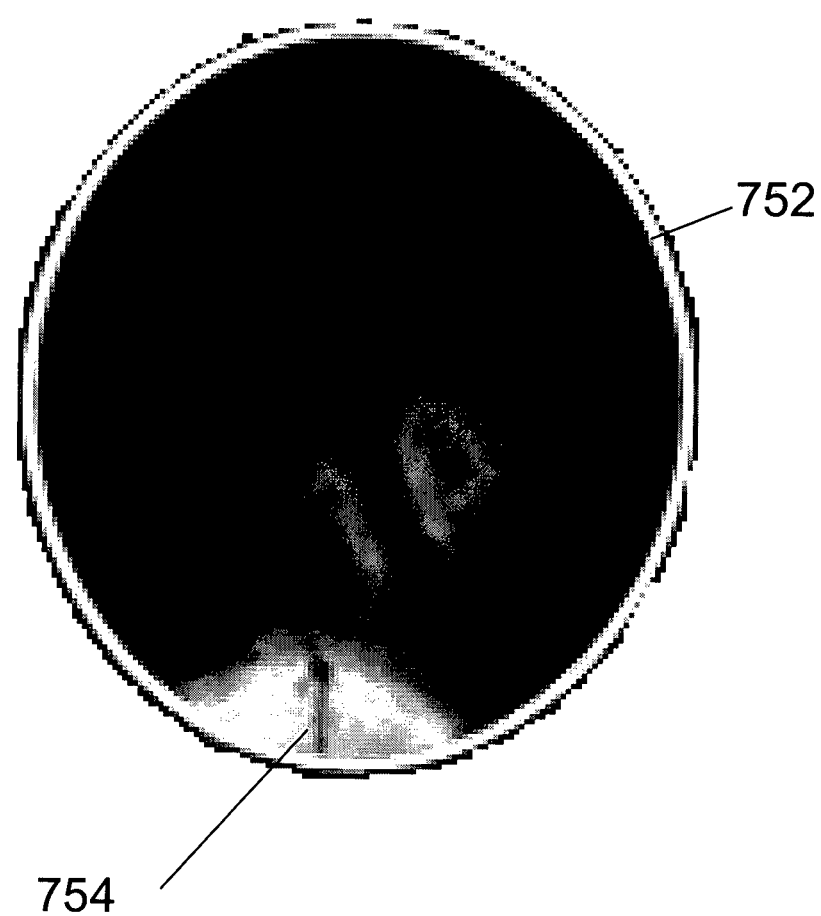
FIG. 7C is a photo seen by the fiberscope when the device, according to various embodiments, is placed in a dark canal.

A guiding arrow (e.g. a red guiding arrow) may be superimposed on the inspection view of the display to provide an augmented view of the cutting tool 210. The guiding arrow may be superimposed by image processing software. The arrow facilitates the surgeon or operator to see and move the operable portion 202 for instance within the ear canal and especially when the operable portion 202 approaches the ear drum. FIG. 7B shows a photo 700b seen by the fiberscope 214, 704 when the device according to various embodiments is placed in an room environment. FIG. 7C shows a photo 700c seen by the fiberscope 214, 704 when the device according to various embodiments is placed in a dark canal. The circle 752 shows the view seen by the fiberscope 214, 704. The guiding arrow 754 indicates the tip of the cutting tool. The bright white parabolic part at the bottom of the view 752 and which is labeled by the guiding arrow 754 is the cutting tool tip.

The fiberscope or endoscope 214, 704 (e.g. ear endoscope) may act as the surgeon's or operator's eye during surgery. It may not be viable to view parts of the human or animal body (e.g. ear membrane) through an external microscope. For instance the operable portion 202 may be inside the ear canal and it may not be feasible to view of the ear membrane using the external microscope. Also, an external microscope may be expensive for an office-based procedure. It may not be viable to insert an otoscope into the ear at the same time as the operable portion 202 due to space and view constraints. Various embodiments allow a viewing mechanism to be fused into the operable portion 202 without taking additional space.

In various embodiments, the operable portion 202 may include a telescopic design including the holder 208, the cutting tool 210 and the fiberscope 214. In various embodiments, the length of the holder 208 may be substantially parallel to the length of the cutting tool 210 and the length of the fiberscope 214.

In various embodiments, the operable portion 202 may further include a suction channel. The suction channel may allow aspiration of fluid accumulated in the human or animal body, for instance in the middle ear. The suction channel may be arranged in the hollow channel of the cutting tool 210.

In various embodiments, the actuator mechanism 204 may include an actuator to move the operable portion along the first axis. In various embodiments, the actuator mechanism 204 may include a further actuator to move or vibrate the operable portion along the second axis. The second axis may be substantially perpendicular to the first axis. The first axis may be the z-axis. The second axis may be the x-axis. The actuator and the further actuator may make up or be included in a two degree of freedom (2-DOF) stage 216. In other words, the actuator mechanism 204 may include a 2-DOF stage 216. The 2-DOF stage 216 may be configured to move the operable portion 202 along the first axis and along the second axis substantially perpendicular to the first axis. The 2-DOF stage 206 may include an actuator and a further actuator.

The 2-DOF stage 216 may be configured to move the operable portion 202 along the first axis and along the second axis at the same time. The 2-DOF-stage 216 may additionally or alternatively be configured to move the operable portion 202 only along the first axis or only along the second axis sequentially.

Incision (e.g. myringotomy) and insertion of the implant (e.g. grommet) may require the movements of the operable portion 202 to be accurate, fast and controllable. In addition, for myringotomy and insertion of grommet, challenges include limited ear canal space and small insertion area on the ear membrane or ear drum. The actuator and/or the further actuator may be or may include piezoelectric actuators (PAs) and/or piezoelectric motors (PMs). Piezoelectric actuators (PAs) and piezoelectric motors (PMs) may offer the advantages of high accuracy, fast response, high speed and resolution compared to manual procedures. PAs/PMs operate based on the piezoelectric effect. The piezoelectric effect is the linear electromechanical interaction between the mechanical and the electrical state in crystalline materials. PAs/PMs may include ultrasonic motors (USMs). The motions of an USM may be converted from the high-frequency mechanical oscillations (generated by the piezoelectric material) by the friction forces between the surface of the stator and rotor of the USM. The USM may generate a longer stroke or travelling range by the sum of the small high-frequency piezoelectric motions compared to other PAs/PMs (which generate motions directly via deformation of the piezoelectric material. In other words, USMs use resonance to amplify the vibration of the stator in contact with the rotor. USMs also offer arbitrarily large rotation or sliding distances, while other piezoelectric actuators are limited by the static strain that may be induced in the piezoelectric element.

In various embodiments, the actuator may be or may include a USM. The further actuator may be or may include a further USM. The 2-DOF stage 216 including the two USMs may be used to generate highly precise motions of the operable portion 202 for operations such as myringotomy and grommet insertion.

In various embodiments, the actuator mechanism may follow a motion sequence or motion profile commands for incision and/or implant insertion. The motion sequence or motion profile commands may be predetermined or preprogrammed. The motion sequence or motion profile commands may be stored in a processor or memory coupled to the actuator mechanism. The motion sequence or motion profile commands may be a according to a predetermined method, e.g. a computer algorithm or software.

Figure 8:
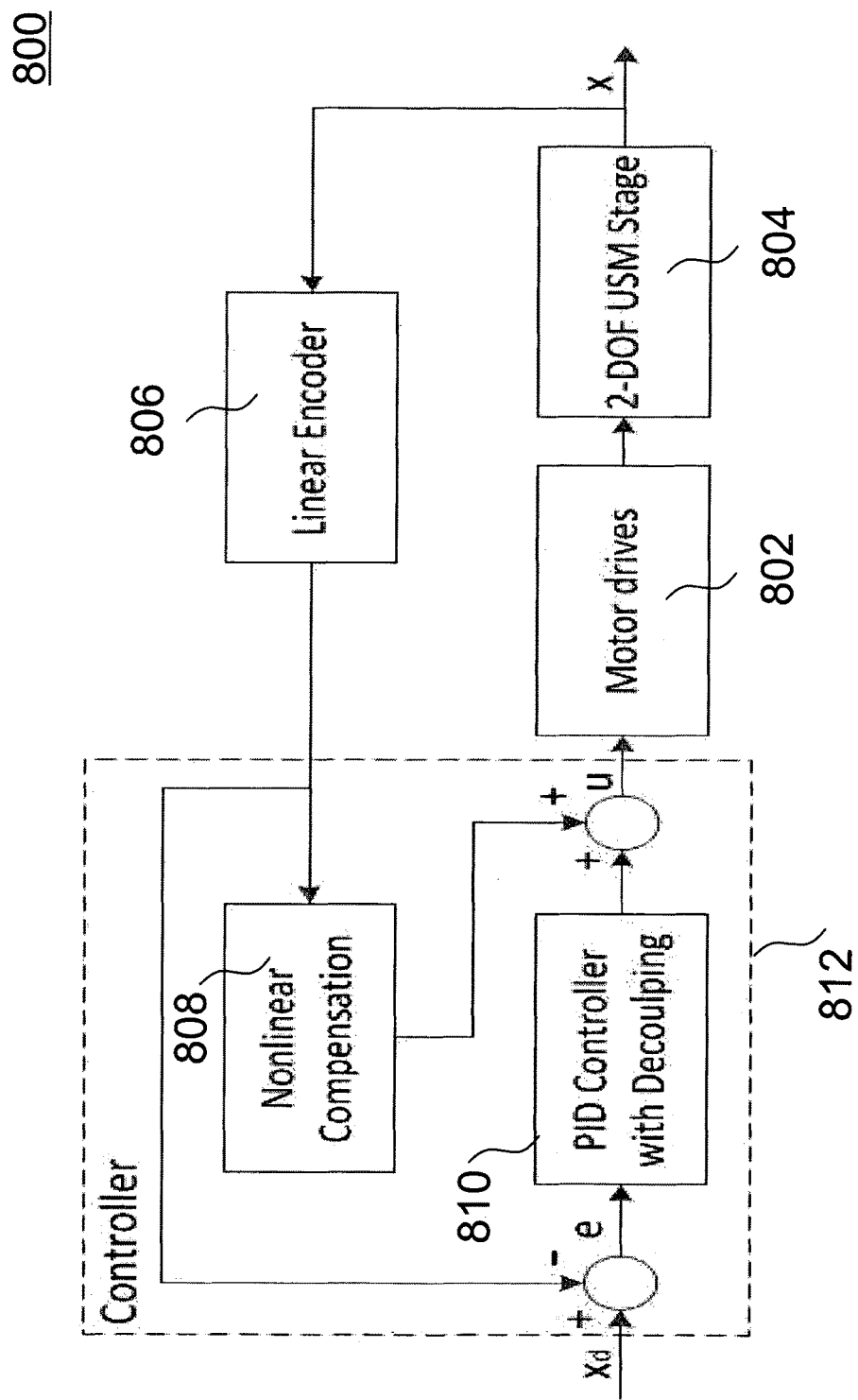
FIG. 8 shows a block diagram of a two-degrees of freedom (DOF) stage coupled to a feedback control system according to various embodiments.

The actuator and further actuator such as the USMs may have non-linear effects. The USMs include piezoelectric materials, which may give rise to the non-linear hysteretic phenomenon. Friction is a main cause of non-linearity in USMs. Also, when two actuators are included to construct or set up a 2-DOF stage 216, coupling phenomenon may arise if the installation is not perfect between the first actuator and the further actuator or if the center-of-gravity position of the load is not exactly at the center of the stage. FIG. 8 shows a block diagram 800 of a two-DOF stage 804 coupled to a feedback control system according to various embodiments. The two actuator or motor drives 802 are used to move the 2-DOF stage 804 for moving the operable portion. A linear encoder 806 may be used to detect the output of the 2-DOF stage 804 and convert the mechanical movement of the 2-DOF stage 804 to electrical signals. The linear encoder may be coupled to a motion controller 812. The motion controller 812 may be a Linear Quadratic Regulator (LQR) based proportional-integral-derivative (PID) controller. The motion controller 812 may include a linear compensation function or module 808 configured to compensate the non-linear forces and uncertainties. A first compensation may be added to eliminate the dominant Coulomb friction while a second compensation based on sliding mode control law may be used to reduce the uncertain friction. The motion controller 812 may further include a decoupling controller 812 configured to decouple the dynamics of the two piezoelectric stages.

Figure 9:
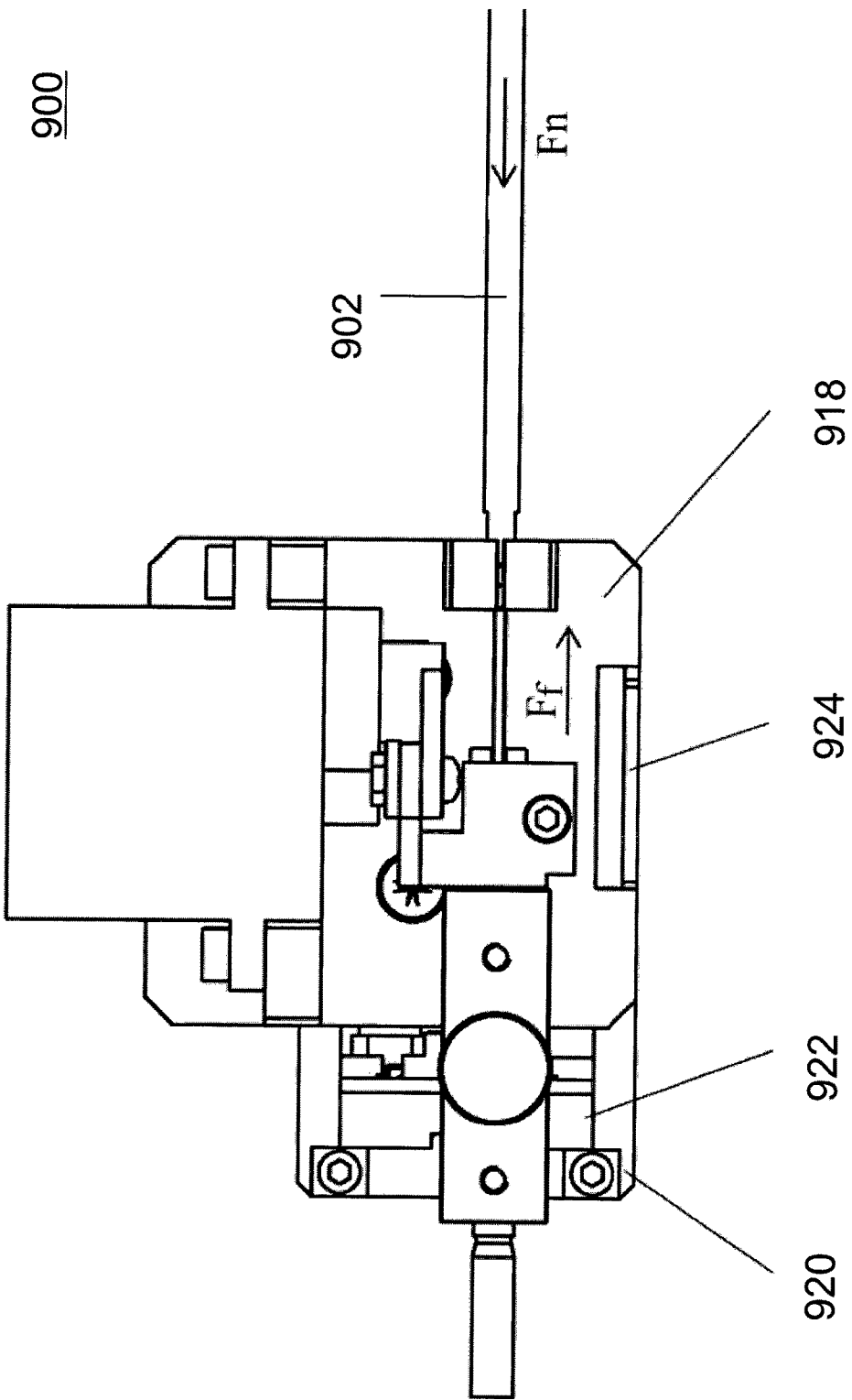
FIG. 9 shows a top view of the device according to various embodiments.

FIG. 9 shows a top view of the device according to various embodiments. The device may include a fixed portion 920. The fixed portion 920 may correspond to the fixed portion 220 in FIGS. 2A-D. The device may further include a movable portion 218, 918. The moving portion 918 may correspond to the moving portion 218 in FIGS. 2A-D. The movable portion 218, 918 may be a moving base. The device may further include a fixed portion 220, 920. The fixed portion 220, 920 may be a fixed plate. The device may be configured such that the movable portion 218, 918 may be moved relative to the fixed portion 220, 920. The operable portion 202, 902 may be mounted on the movable portion 218, 918. The device may include a guideway between the fixed portion 220, 920 and the movable portion 218, 918 for reducing friction when the movable portion 218, 918 is moved relative to the fixed portion 220, 920. The device may further include a force sensor 922 (corresponding to force sensor 222 in FIGS. 2A-D) coupled between the fixed portion 220, 920 and the movable portion 218, 918. The force sensor 222, 922 may be on the fixed portion 220, 920 while the probe of the force sensor 222, 922 may be attached to the movable portion 218, 918.

The device may further include slide locks 924 corresponding to slide locks 224 in FIGS. 2A-D) such that the movable portion 218, 918 may only be moved along the first axis (e.g. z-axis). The slide locks 224, 924 may be configured to allow the movable portion 218, 918 to move only in the negative z axis direction when the operable portion 202, 902 is in the second position. The slide locks 224, 924, may be further configured to allow the movable portion 218, 918 to move only in the positive z axis direction when the operable portion 202, 902 is in the first position. The force sensor 222, 922 may be configured to measure the force applied to the movable portion 218, 918 along the first axis (z axis).

As the cutting tool 210 and the holder 208 are unable to move relative to the movable portion 218, 918 (since the cutting tool 210 and the holder 208 are mounted on the movable portion 218, 918), the cutting tool 210, the holder 208 and the movable portion 218, 918 may be considered as a rigid body. When a force is applied to the cutting tool 210 and/or the holder 208, the force may be transmitted to the force sensor 222, 922 to be measured. The measured force, $F_m$, may be provided by the following equation:

$$F_m = F_n - F_f \qquad (2)$$

where $F_m$ is the measured force, $F_n$ is the applied force and $F_f$ is the friction. As the guideway reduces friction $F_f$ to be negligible, Equation (2) may be simplified as:

$$F_m \approx F_n \qquad (3)$$

The force sensor 222, 922 may complement vision sensing. The force sensor 222, 922 may alert the surgeon or operator to key instances such as contact of the device with the human or animal body as well as the making of the incision.

FIGS. 10A-J shows a method of using the device to insert an implant 1006 into a human or animal body according to various embodiments. In various embodiments, the incision may be made on an ear membrane (also referred to as an ear drum membrane). The implant 1006 may be inserted at least partially through the incision on the ear membrane. The implant 1006 may be a grommet.

The method may include using the device to insert the implant 1006 at least partially through the incision on the human or animal body. The method may include operating the device to move the operable portion 1002 of the device along the second axis. The method may also include operating the device to move the operable portion 1002 of the device along the first axis. Movement of the operable portion 1002 along the first axis and the second axis may be carried out sequentially or simultaneously.

Figure 10A:
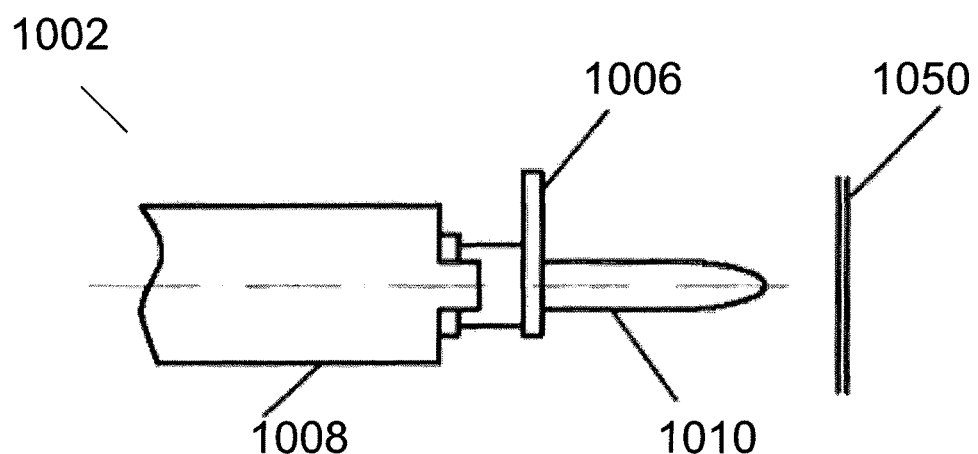
Figure 10B:
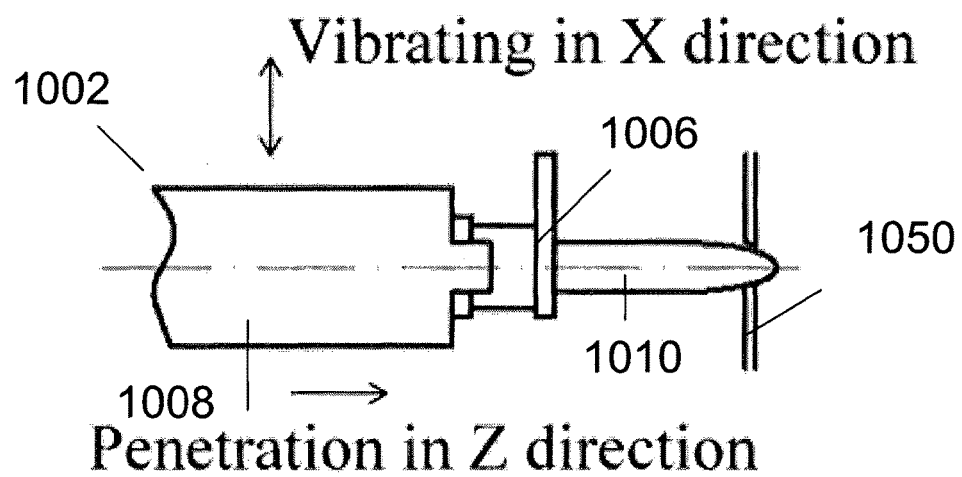

FIG. 10A is a side view 1000a of a operable portion 1002 of the device with an implant 1006 such as a grommet according to various embodiments. The operable portion 1002 may include a holder 1008. The operable portion 1002 may further include a cutting tool 1010. The implant may be implanted on a body part 1050 such as an ear drum membrane. The implant 1006 may be engaged or held by the cutting tool 1010. The cutting tool 1010 may pass through a hole of the implant 1006 to engage or hold the implant 1006. The incision and insertion location may be selected by a person such as a surgeon with the help of the fiberscope which yield an image of the body part 1050. The operable portion may then be adjusted manually or automatically (along the second axis) so that the tip of the cutting tool is pointing at the desired incision and insertion location. The fiberscope may help in the adjustment. The person may use the fiberscope to look for the desired incision and insertion point. Movement of the operable portion 1002 along the second axis may be due to an actuator mechanism coupled to the operable portion 1002. The operable portion 1002 may be advanced until the operable portion 1002 touches the body part 1050 at a contact point. The operable portion 1002 may be moved along the first axis by the actuator mechanism coupled to the operable portion 1002. The actuator mechanism may include an actuator to move the operable portion 1002 along the first axis. The actuator mechanism may also include a further actuator to move the operable portion 1002 along the second axis. The touching of the body part 1050 by the operable portion 1002 (i.e. the tip of the cutting tool 1010) may be detected by the force sensor. FIG. 10B is a side view 1000b showing the incision of the body part 1050 (e.g. myringotomy) using the cutting tool 1010 according to various embodiments. The method may include operating the device to move the operable portion 1002 of the device along a first axis and move or vibrate the operable portion of the device along a second axis perpendicular to the first axis to make an incision on the human or animal body. The incision may be made by the cutting tool 1010. Moving along the first axis and along the second axis may be carried out simultaneously, i.e. at the same time. Moving along the second axis may include vibrating at a predetermined frequency. The penetration displacement of the tip of the cutting tool 1010 from the contact point may be less than 2 mm. The penetration displacement may be limited to that the tip of the cutting tool 1010 may not hurt the inner parts of the body (such as the inner ear). The incision dimensions may be created according to the dimensions of the implant. A whole range of implants or standard grommets of varying dimensions may be accommodated.

Figure 10C:
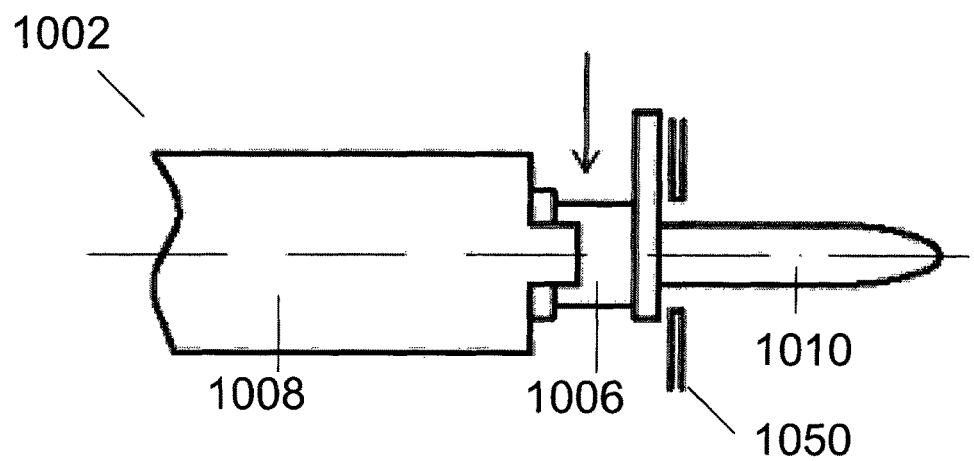
Figure 10D:
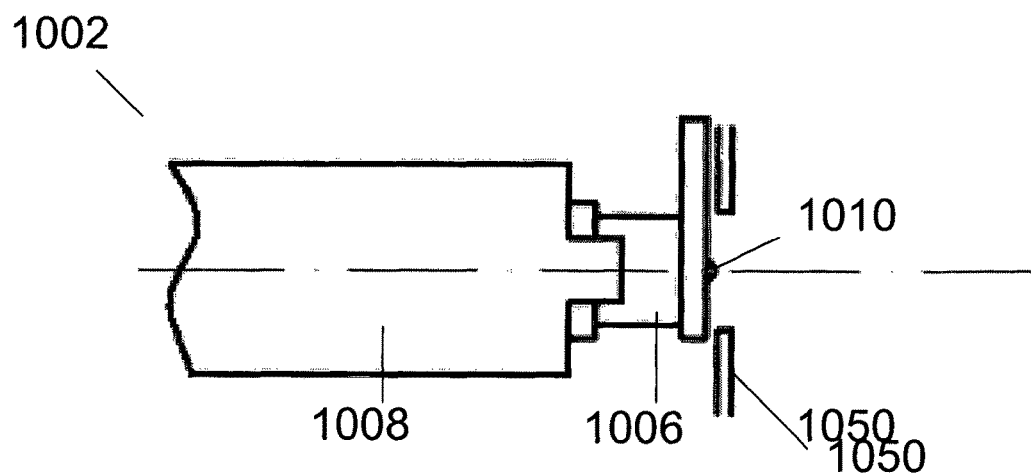

FIG. 10C is a side view 1000c showing the continued incision of the body part 1050 for insertion of the implant 1010 according to various embodiments. The method may include operating the device to move the operable portion 1002 of the device along the first axis until the force sensor detects that the implant is in contact with the body part 1050. FIG. 10D is a side view 1000d showing the retraction of the cutting tool 1010 according to various embodiments. The cutting tool 1010 may be configured to move between a first position, a second position or an intermediate position between the first position and the second position. The cutting tool 1010 may be received in the cavity of the elongated holder 1008 when the cutting tool is in the first position. The cutting tool 1010 may be protruded from the cavity of the elongated holder 1008 for making the incision on the human or animal body when the cutting tool 1010 is in the second position. The cutting tool 1010 may be partially received in the cavity of the elongated holder 1008 such that the implant 1010 is held or engaged by the cutting tool and the cutting tool 1010 does not protrude from the implant 1010 when the cutting tool 1010 is in the intermediate position. The method may include retracting the cutting tool 1010 from the second position to the intermediate position. The cutting tool 1010 may be partially received in the elongated holder 1008 when the cutting tool is in the intermediate position. When the cutting tool 1010 is in the intermediate position, the cutting tool 1010 may still hold the implant 1006. The cutting tool 1010 may be moved from the second position to the first position or the intermediate position using a cutter retraction mechanism. The distance of the intermediate position from the second position may be just enough to prevent damage or hurt to other body parts (e.g. the middle ear) when the implant (e.g. grommet) is pushed forward in the subsequent steps.

Figure 10E:
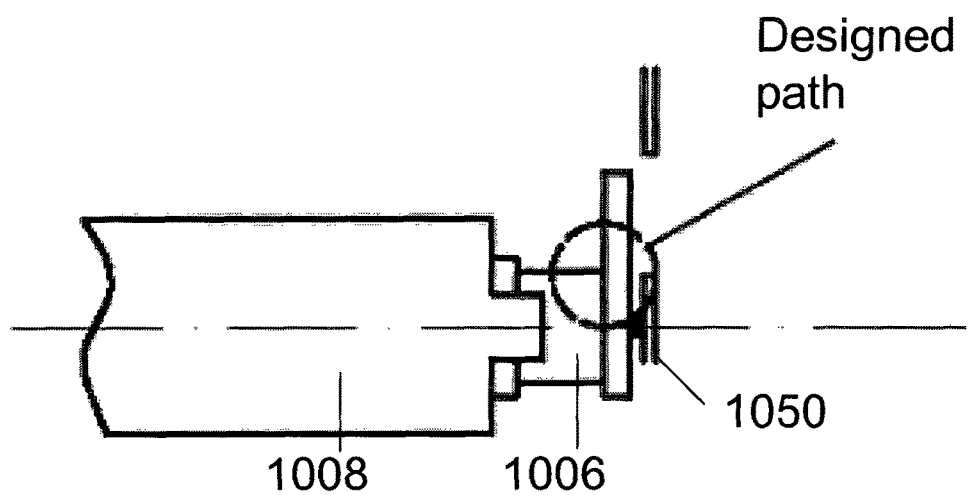
Figure 10F:
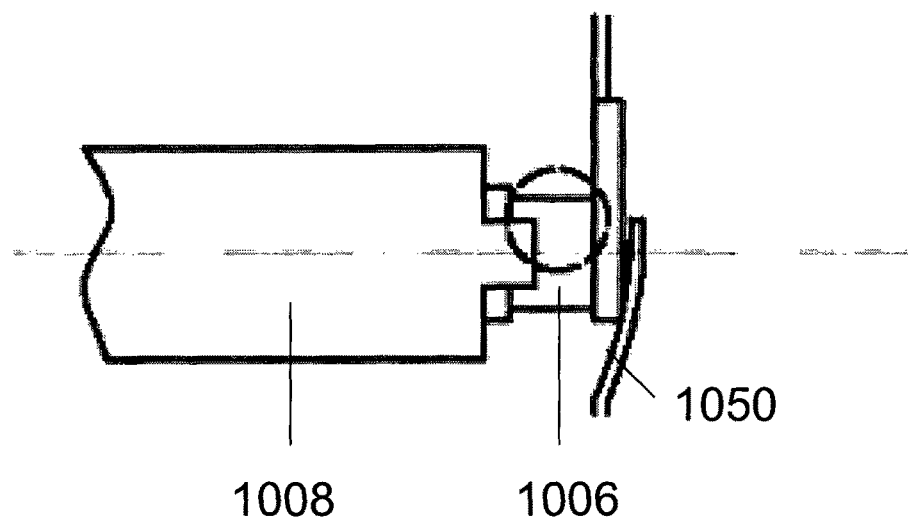
Figure 10G:
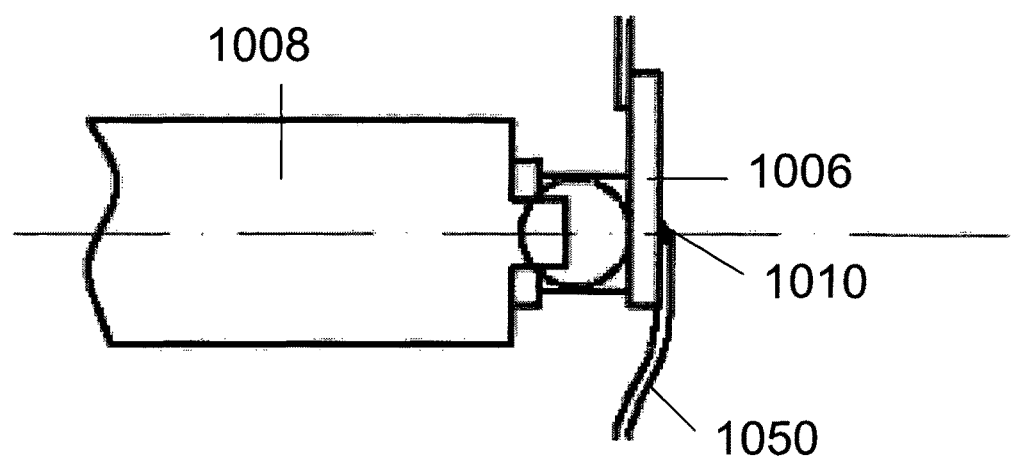
Figure 10H:
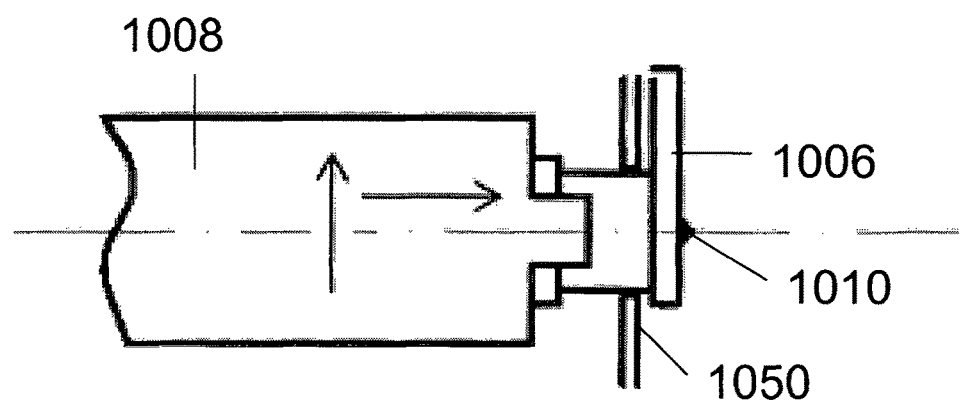

FIG. 10E is a side view 1000e showing the insertion of the implant 1006 as the operable portion 1002 is moved along the second axis according to various embodiments. FIG. 10F is a side view 1000f showing the continued insertion of the implant 1006 as the operable portion 1002 is moved along the first axis according to various embodiments. FIG. 10G is a side view 1000g showing the continued insertion of the implant 1006 as the operable portion 1002 is moved along the second axis in a direction opposite to the direction moved by the operable portion 1002 in FIG. 10E according to various embodiments. A portion of the implant 1006 is inserted in the incision. A portion of the implant such a long portion or end of the implant 1006 may be first inserted in the incision. The implant may be woven into the body part 1050 (e.g. ear drum membrane) along a quarter circle path. FIG. 10H is a side view 1000h showing the implant 1006 fully inserted in the incision according to various embodiments. The operable portion 1002 may be configured to move along the first axis and then along the second axis in a first sequence or configured to move along the second axis and then along the first axis in a second sequence to fully insert the implant 1006. In other words, the full insertion of the implant may require two short steps.

Figure 10I:
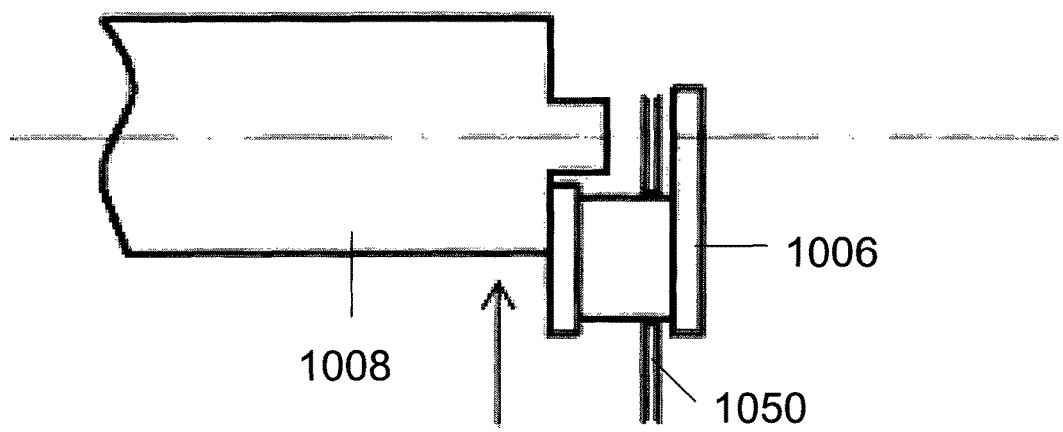
Figure 10J:
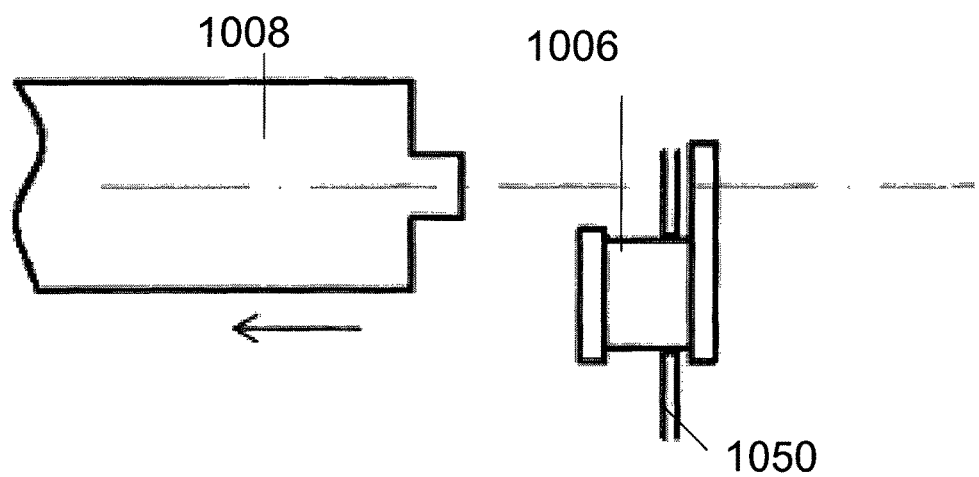

The method may include retracting the cutting tool 1010 from the intermediate position to the first position. The movement of the cutting tool 1010 from the intermediate position to the first position may bar carried out upon insertion of the implant 1006 through the incision. FIG. 10I is a side view 1000g showing the continued insertion of the implant 1006. The method may further include operating the device such that the operable portion 1002 is disengaged from the implant 1006 after the implant 1006 is fully or at least partially inserted through the incision. The operable portion 1002 may be moved along the second axis such that the implant 1006 is disengaged from the plurality of claws on the first end of the holder 1008. FIG. 10J is a side view 1000j showing the withdrawing of the operable portion 1006 after the implant 1006 is fully or at least partially inserted through the incision. The operable portion 1006 may be moved along the first axis after the implant 1006 is disengaged from the plurality of claws on the first end of the holder 1008. A part of the method may be automatic. For instance, using the device to make an incision on the human or animal body may be automatic. Using the device to insert the implant 1006 at least partially through the incision on the human or animal body may be automatic. Further, using the device to disengage or dislodge the implant 1006 from the operable portion 1002 and/or the withdrawing of the operable portion 1002 after disengagement or dislodgement may also be automatic.

The movement of the operable portion 1002 may be controlled by the actuator and the further actuator. The actuator may control the movement of the operable portion 1002 along the first axis. The further actuator may control the movement of the operable portion 1002 along the second axis. The movement of the cutting tool 1010 along the holder 1008 may be controlled by a cutter retraction mechanism. In other words, the movement of the cutting tool 1010 between a first position, a second position and an intermediate position between the first position and the second position may be controlled by the cutter retraction mechanism. The cutter retraction mechanism may include a servo motor.

In various embodiments, the method may include operating the device to move the operable portion 1002 of the device along a first axis and to vibrate the operable portion 1002 of the device along a second axis perpendicular to the first axis simultaneously to make an incision on the human or animal body. The vibration of the operable portion 1002 along the second axis may be at a predetermined frequency or set of frequencies. Vibration of the operable portion 1002 of the device along the second axis may be at a frequency or set of frequencies above about 3 Hz, or above about 5 Hz, or above about 10 Hz, or above about 20 Hz or above about 30 Hz or between about 3 Hz to about 50 Hz, e.g. between about 5 Hz to about 40 Hz, e.g. between about 20 Hz to about 30 Hz, e.g. about 30 Hz. FIG. Vibrating the operable portion 1002 along the second axis while moving the operable portion 1002 along the first axis to make the incision may increase speed without losing precision and/or reduce deformation of the body part such as ear drum membrane and reduce trauma to the patient.

Figure 11B:
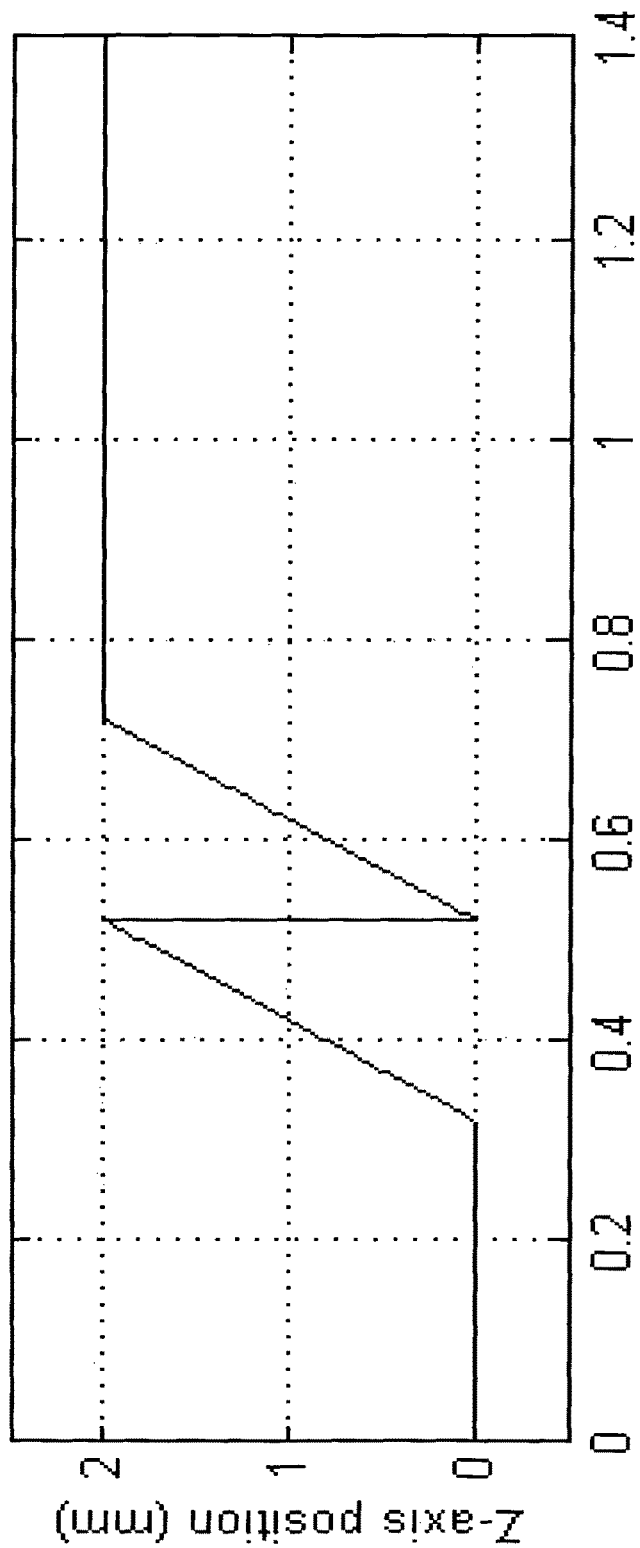
FIG. 11B is a graph of the displacement of the operable portion along the first axis as a function of time when making an incision according to various embodiments.
Figure 11C:
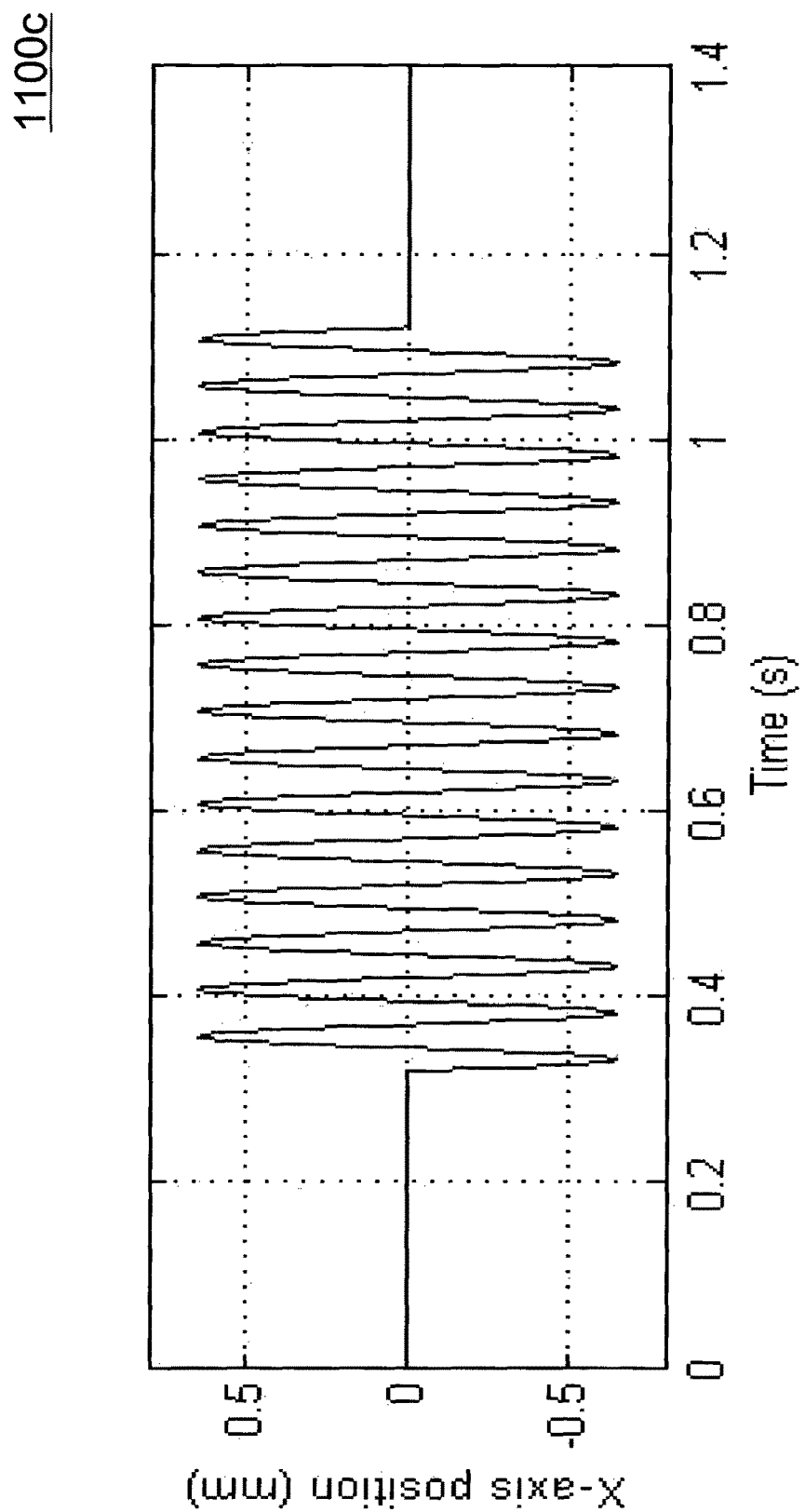
FIG. 11C is a graph of the displacement of the operable portion along the second axis as a function of time when making an incision according to various embodiments.
Figure 11D:
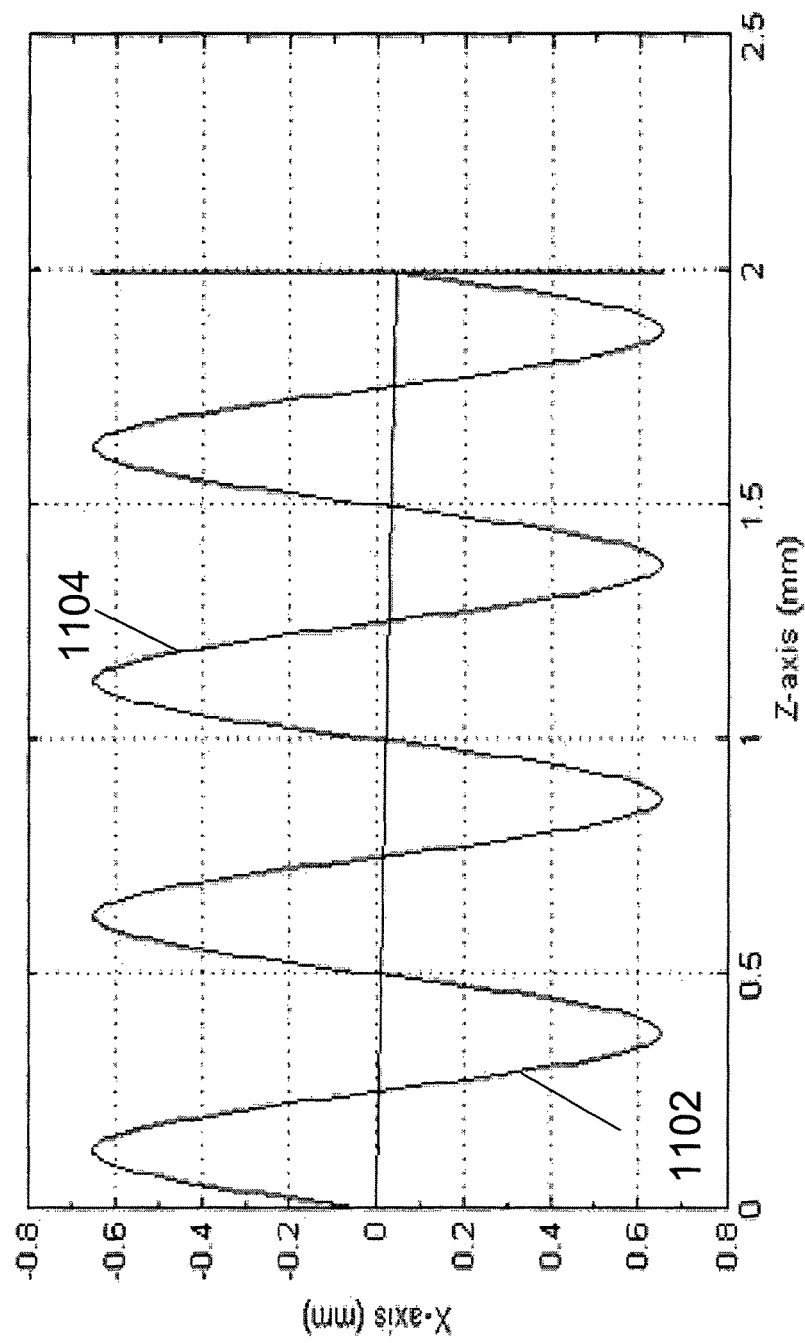
FIG. 11D shows a graph of the displacement of the operable portion along the second axis as a function of the displacement of the operable portion along the first axis when making the incision according to various embodiments.

For instance, the ear membrane may not be penetrated solely by moving the cutting tool 1010 by a small movement of 0.2 mm (which extends beyond the thickness of the membrane) along the first axis as the ear membrane is elastic. However, a larger displacement along the first axis may result in a large deformation of the membrane which will lead to discomfort of the patient or even tear the membrane. Vibrating the operable portion 1002 along the second axis at the same time as moving the operable portion 1002 along the first axis to penetrate the body part such as ear drum membrane may allow the incision to be achieved at a faster rate without inducing much deformation. FIG. 11A shows a table 1100a of the time taken to make the incision when vibrating the operable portion 1002 at different frequencies along the second axis according to various embodiments. The results shown in FIG. 11A shows that the higher the frequency of vibration, the shorter the time for the incision to be made. FIG. 11B shows a graph 1100b of the displacement of the operable portion 1002 along the first axis as a function of time when making an incision according to various embodiments. FIG. 11C shows a graph 1100c of the displacement of the operable portion 1002 along the second axis as a function of time when making an incision according to various embodiments. FIG. 11D shows a graph 1100d of the displacement of the operable portion. 1002 along the second axis as a function of the displacement of the operable portion 1002 along the first axis when making the incision according to various embodiments. Line 1102 indicates the actual displacement along the second axis as a function of the displacement along the first axis while line 1104 indicates the averaged displacement of the operable portion 1002 along the second axis as a function of the displacement of the operable portion 1002 along the first axis. In various embodiments, the actuator mechanism may be configured to move the operable portion along the first axis according to a sawtooth profile seen in FIG. 11B. In various embodiments, the actuator mechanism may be configured to move the operable portion along the second axis according to a vibration profile seen in FIG. 11C.

Figure 12A:
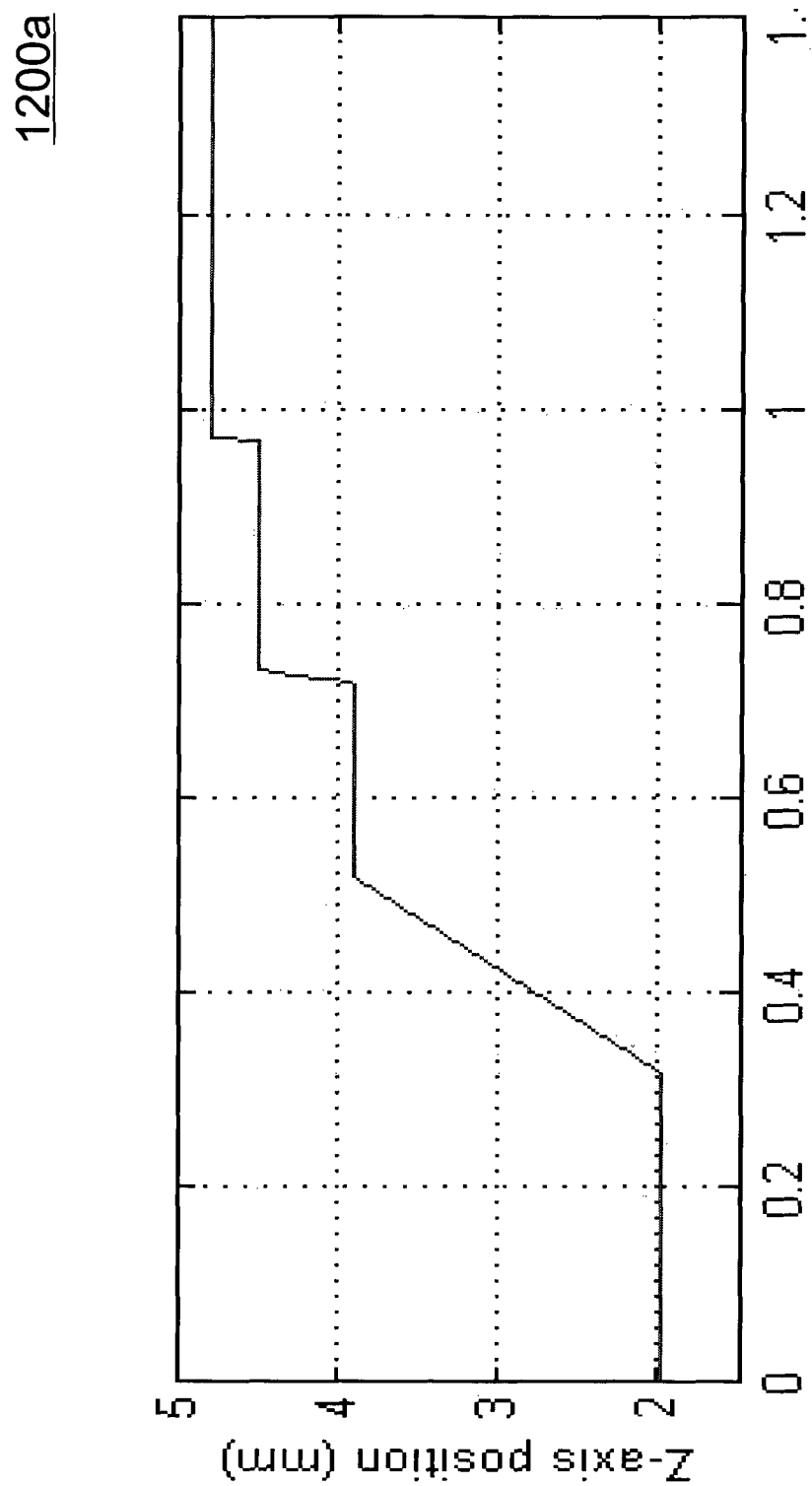
FIG. 12A is a graph of the displacement of the operable portion along the first axis as a function of time when inserting the implant according to various embodiments.
Figure 12B:
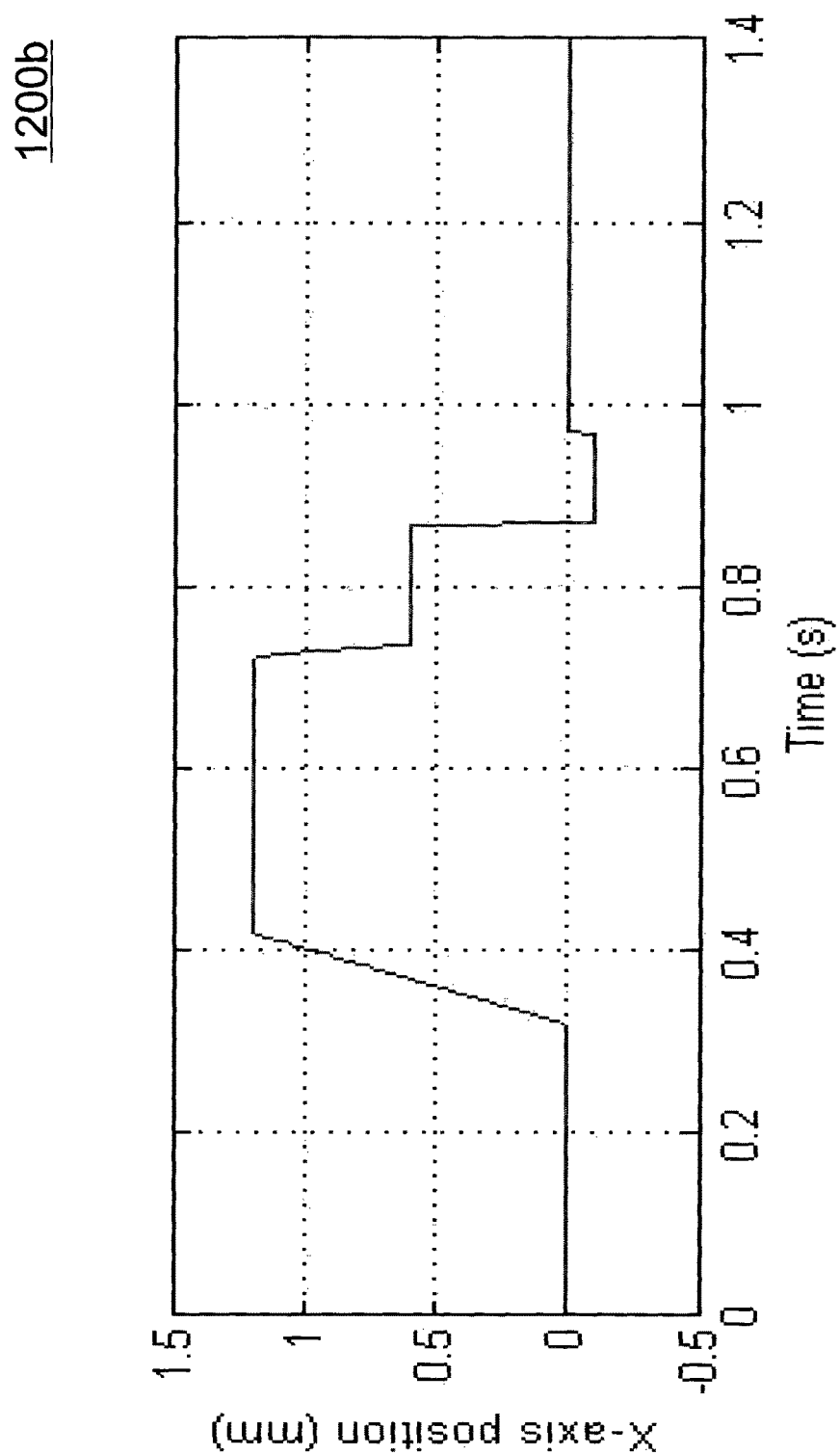
FIG. 12B is a graph of the displacement of the operable portion along the second axis as a function of time when inserting the implant according to various embodiments.
Figure 12C:
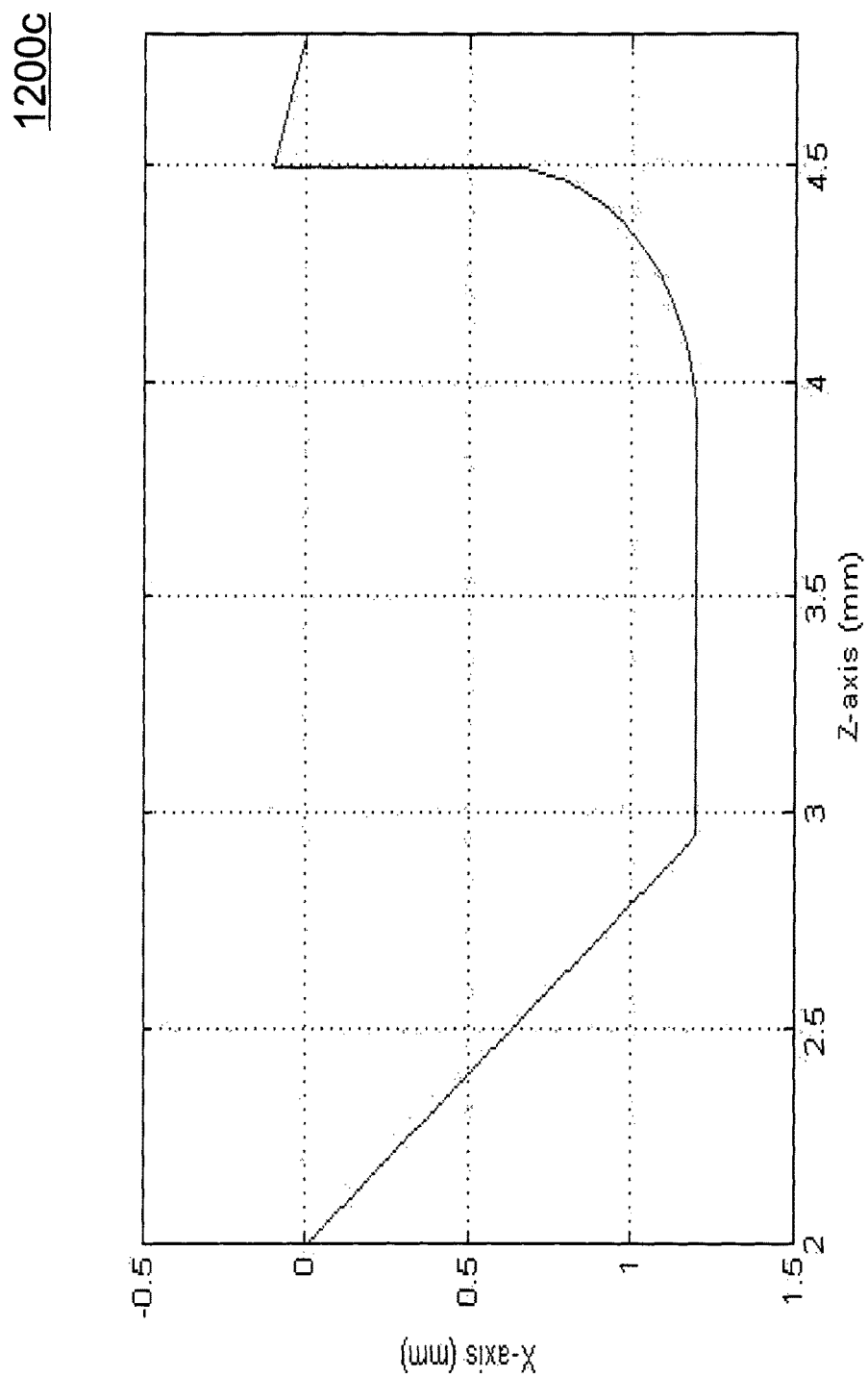
FIG. 12C is a graph of the displacement of the operable portion along the second axis as a function of the displacement of the operable portion along the first axis when inserting the implant according to various embodiments.

In various embodiments, the method may include using the device to insert the implant 1006 at least partially through the incision on the human or animal body. The method may include operating the operable portion 1006 to insert the implant 1006 at least partially through the incision on the human or animal body. FIG. 12A shows a graph 1200a of the displacement of the operable portion 1002 along the first axis as a function of time when inserting the implant 1006 according to various embodiments. FIG. 12B shows a graph 1200b of the displacement of the operable portion 1002 along the second axis as a function of time when inserting the implant 1006 according to various embodiments. FIG. 12C shows a graph 1200c of the displacement of the operable portion 1002 along the second axis as a function of the displacement of the operable portion 1002 along the first axis when inserting the implant 1006 according to various embodiments. In various embodiments, the actuator mechanism may follow a motion sequence or motion profile commands for incision and/or implant insertion. The motion sequence or motion profile commands may be predetermined or preprogrammed. The motion sequence or motion profile commands may be stored in a processor or memory coupled to the actuator mechanism.

Figure 13A:
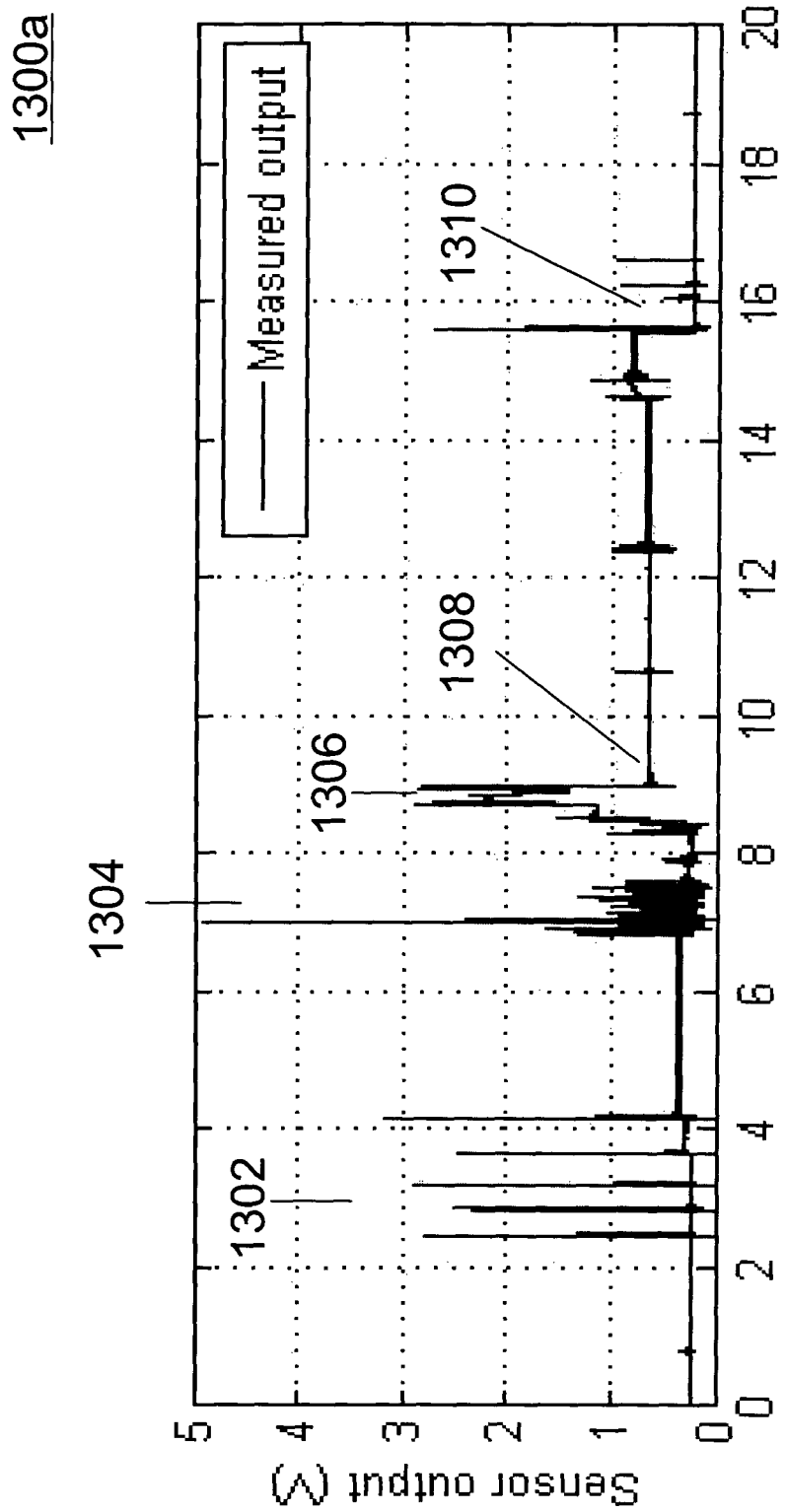
FIG. 13A is a graph illustrating the sensor output as a function of time according to various embodiments.
Figure 13B:
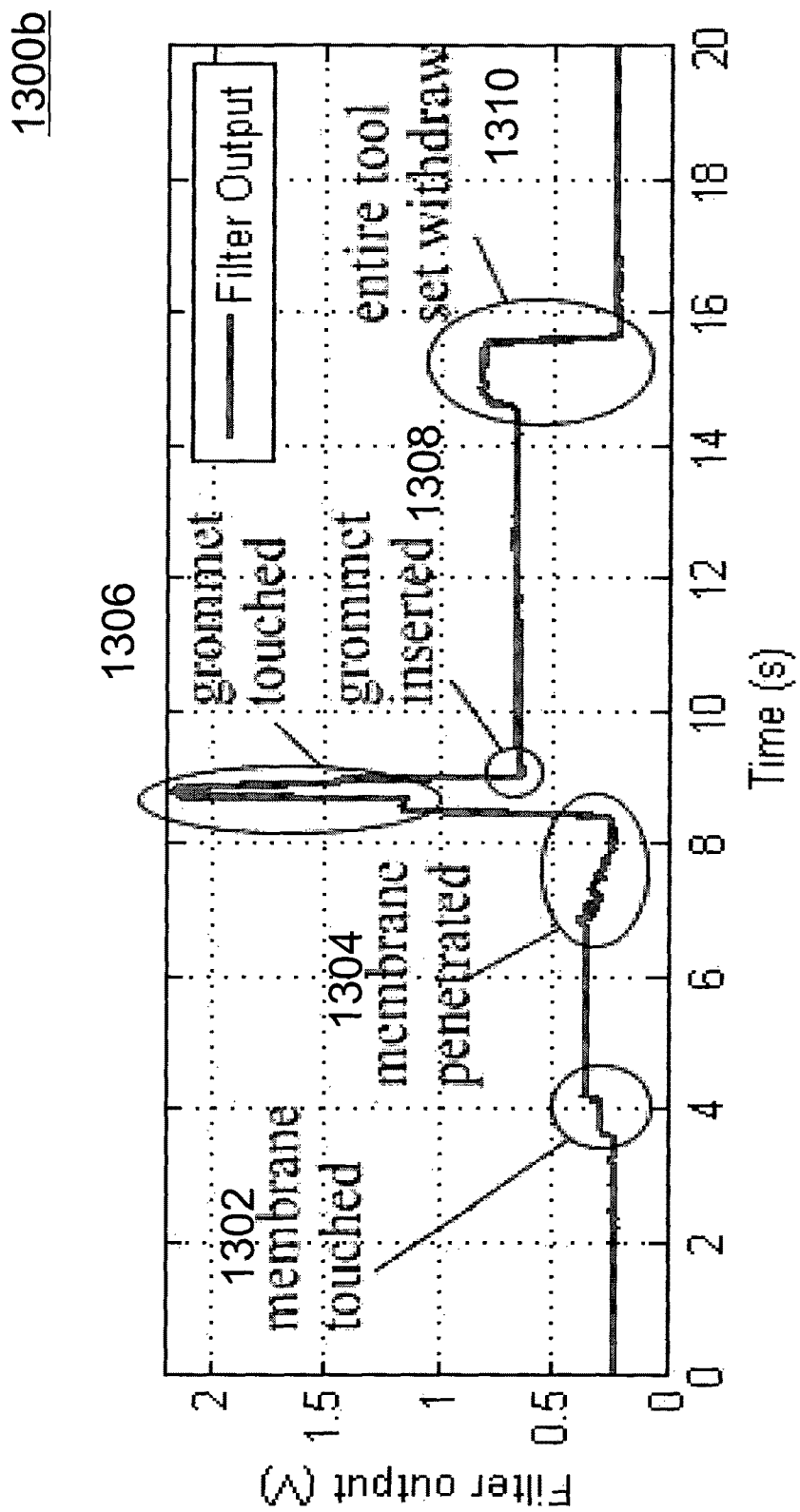
FIG. 13B is a graph illustrating the filtered output as a function of time according to various embodiments.

During the process shown in FIGS. 10A-J, the force $F_m$ detected by the force sensor may vary. In various embodiments, the method includes coupling a force sensor between the fixed portion and the movable portion. The method may include detecting or measuring the force exerted on the operable portion by detecting or measuring the force on the movable portion as the movable portion and the operable portion may be considered as one rigid body. FIG. 13A is a graph 1300a illustrating the sensor output as a function of time according to various embodiments. The sensor output (in volts) is proportional to the force F. detected by the force sensor. FIG. 13B is a graph 1300b illustrating the filtered output as a function of time according to various embodiments. FIGS. 13A and 13B show that the force $F_m$ may vary depending on whether the cutting tool has just touched the body part, i.e. membrane (in 1302), the membrane is penetrated (in 1304), the implant 1006, i.e. grommet, has contacted the body part (in 1306), the implant is inserted through the incision (in 1308) or whether the operable portion (i.e. entire toolset) is withdrawn (in 1310). 1302 and 1304 occurs before the cutting tool is retracted while 1306, 1308 and 1310 occurs after the cutting tool is retracted. When the cutting tool is not retracted, the force sensor may measure the force on the tip of the cutting tool. When the cutting tool is retracted, the force sensor may measure the force on the first end of the holder or on the implant. Various embodiments allow the measurement or detection using only one sensor to determine whether the cutting tool touches the membrane, whether the membrane has been penetrated and whether the grommet is inserted on the membrane. The method may further include identifying the steps the device is carrying out based on the output of the force sensor. The device may be able to trace the current state of the procedure, minimizes process time and/or improve success rate.

The method may further include arranging a fiberscope or an endoscope at least partially within an hollow channel of the cutting tool 1010. The method may include marking out the targeted incision spot on the images obtained by the fiberscope or the endoscope such that the targeted incision spot may be aligned with the guiding arrow. The guiding arrow may be on the tip of the cutting tool 1010. While the surgeon or operator may be able to determine the targeted spot visually, aligning the targeted incision spot with the guiding arrow may alleviate the task and enable the surgeon or the operator to more efficiently accomplish the procedure.

Figure 14A:
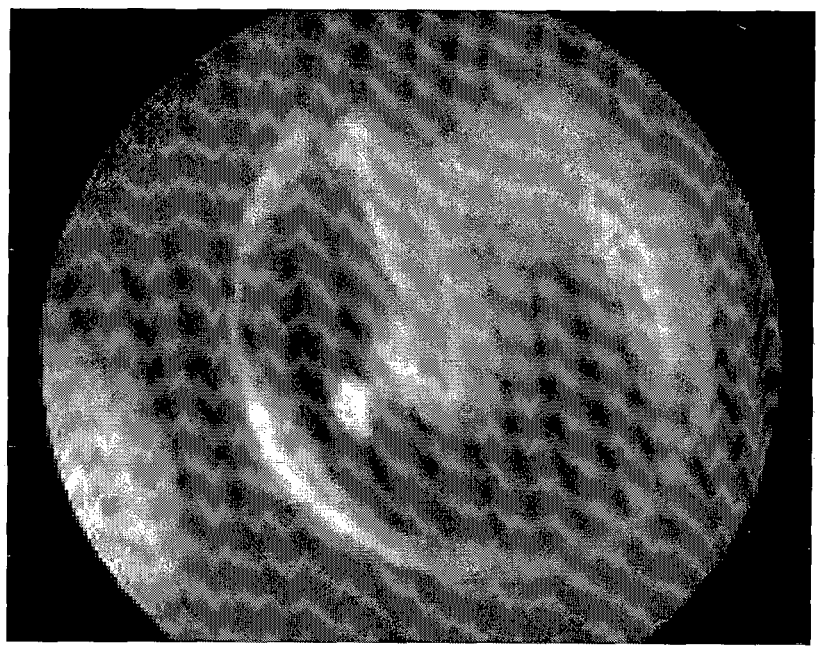
FIG. 14A is an image of an ear membrane taken using an otoscope.

The method may also include comparing the image taken using the fiberscope or endoscope with a reference image. Comparing the image taken using the fiberscope or endoscope with a reference image may be carried out using an image comparison software or algorithm. The method may further include examining the body part, e.g. the ear drum membrane using a examining device such as an otoscope prior to operating the operable portion 1002 of the device. The surgeon or person make examine the body part for diagnostic purpose and may make a determination whether implant insertion using the device is permissible. An image of the body part for implant may be taken. FIG. 14A shows an image 1400a of a ear membrane taken using an otoscope.

Figure 14B:
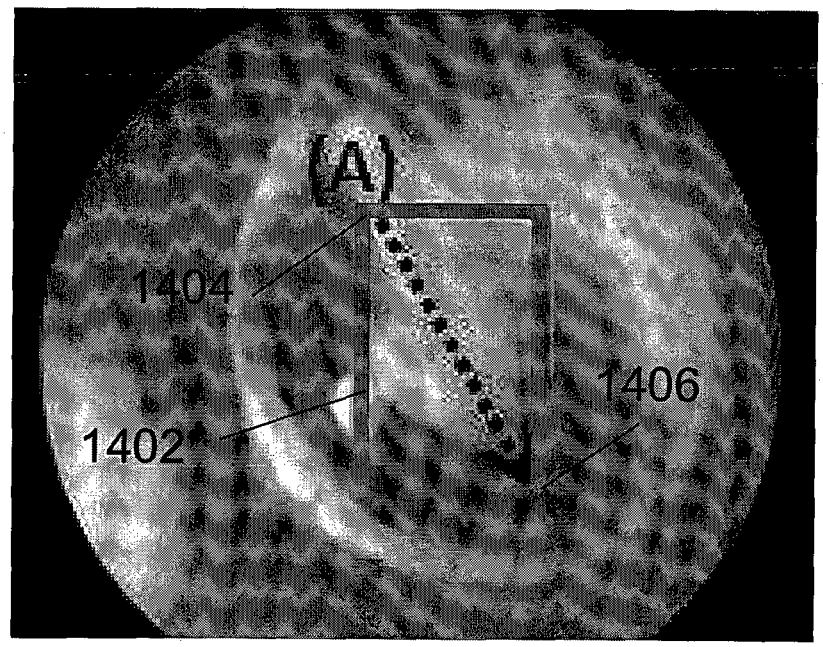
FIG. 14B is the marked image of the reference image shown in FIG. 14A.
Figure 14C:
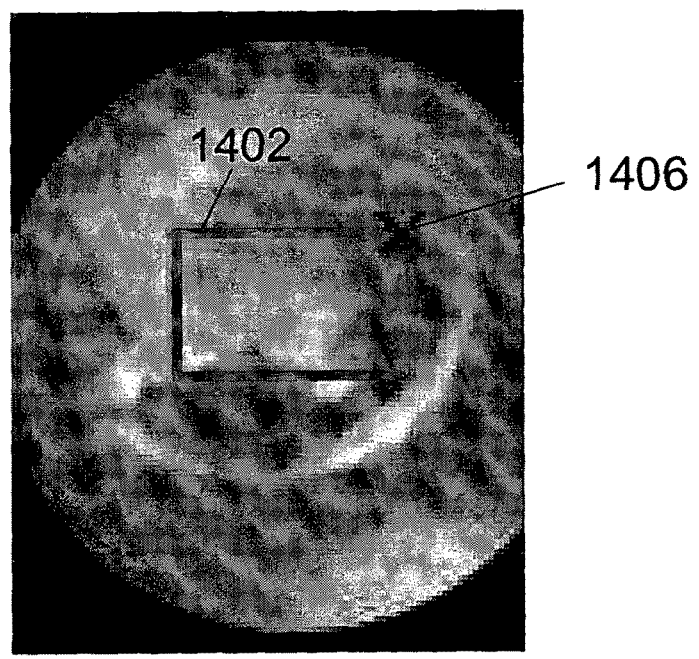
FIG. 14C shows a resized and rotated image of the marked image shown in FIG. 14A.

FIG. 14B shows the marked image 1400b of the reference image 1400a shown in FIG. 14A. The image 1400a may be marked using an image processing software or algorithm. A box 1402 indicating a region of interest may be marked. The box 1402 may be marked by identifying a reference spot 1404 (indicated as A) and defining the box 1402 by using spot 1404 (A) as the top upper corner of the region of interest. The box 1402 may be defined with the targeted incision point (indicated as X) 1404 as the bottom right corner. The marked image 1404 may be rotated and resized for comparison and matching with images obtained from the fiberscope or endoscope. FIG. 14C shows a resized and rotated image 1400c of the marked image 1400b shown in FIG. 14A. The image comparison software or algorithm may be configured such that despite the different sizes and rotational orientation of the image obtained from the fiberscope or endoscope and the reference image, the comparison and matching task may still proceed intelligently. The reference image may be the resized and rotated image 1400c or the marked image 1400b.

During the procedure, images from the fiberscope or endoscope may be compared and matched with the reference image. The comparison and matching may be done using an image comparison software or algorithm. The image comparison software or algorithm may be part of the image processing software or algorithm used to mark the image or the image comparison software or algorithm may be a separate software.

Figure 14D:
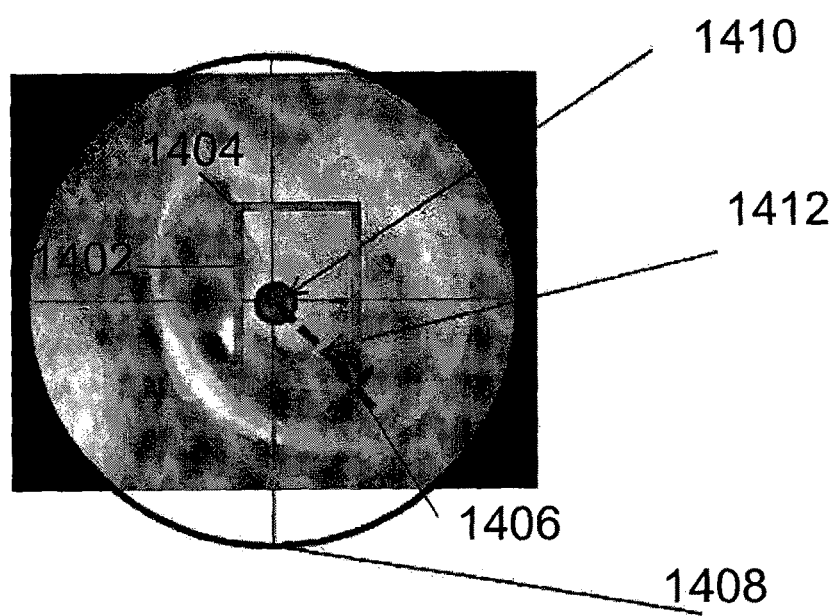
FIG. 14D shows an image obtained from the fiberscope or endoscope (also known as fiberscope view) superimposed with markings on the reference image.
Figure 14E:
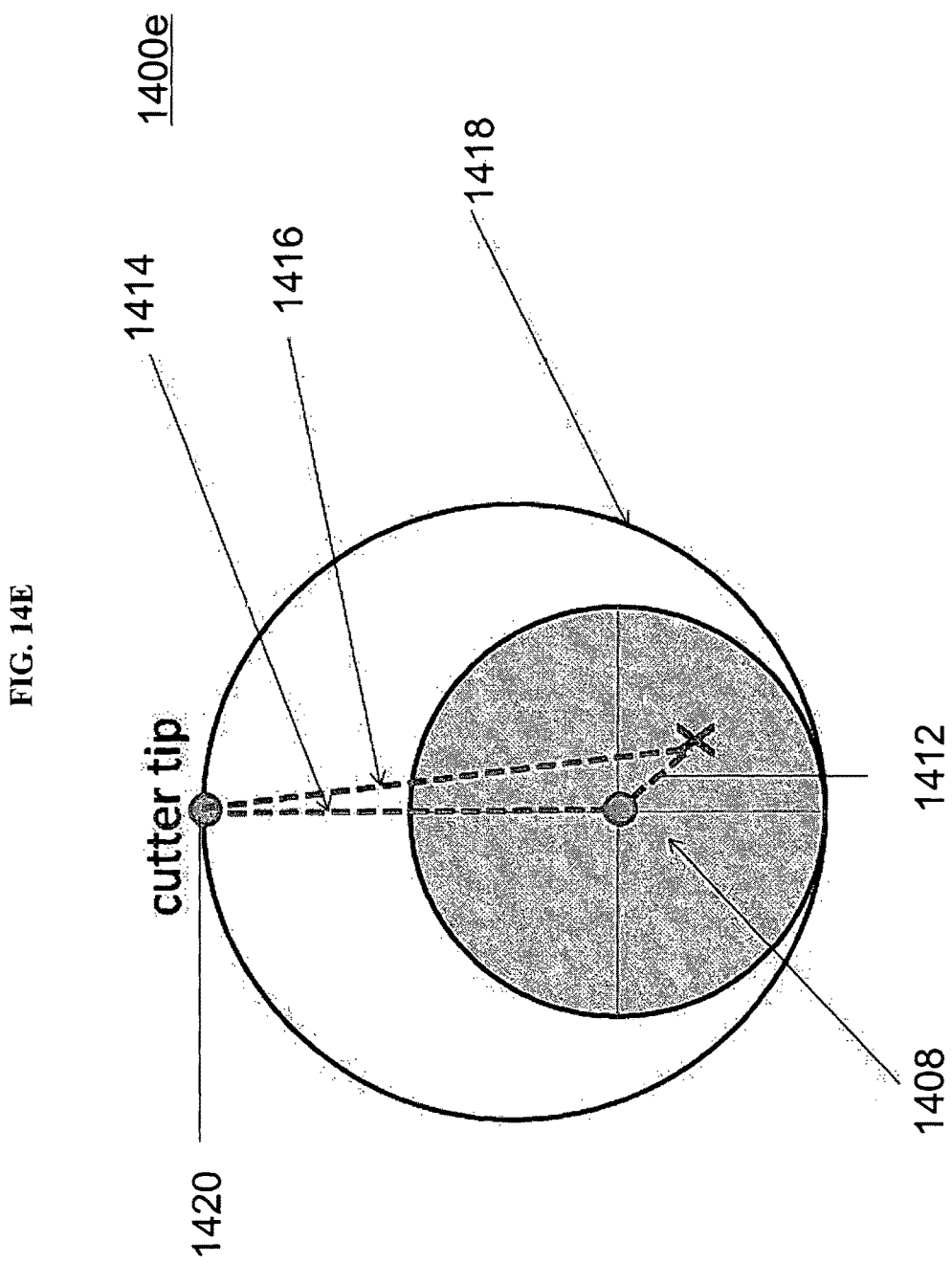
FIG. 14E is a cross-sectional schematic of a fiberscope or endoscope taken from the front of the cutting tool shown in FIG. 7A.

The method may further include comparing the image taken using the fiberscope or endoscope with a reference image to align the tip of the cutting tool with the targeted incision spot 1406. FIG. 14D shows an image obtained from the fiberscope or endoscope (also known as fiberscope view 1408) superimposed with markings on the reference image. The targeted incision spot 1406 may be marked on the reference image. The method may include superposing the markings on the reference image, including the targeted incision spot 1406 on the image obtained from the fiberscope or endoscope (also known as fiberscope view 1408). The method may include calculating a first distance 1412 from the targeted incision spot 1406 to the centre of the fiberscope view 1410. The first distance 1412 may be measured in pixels and converted to real world coordinates. FIG. 14E is a cross-sectional schematic 1400e of a fiberscope or endoscope taken from the front of the cutting tool shown in FIG. 7A. The arrow 750 in FIG. 7A indicates the view corresponding to the schematic 1400e. FIG. 14E shows a cross-section of the fiberscope 1408 arranged in a hollow channel of the cutting tool 1418. The distance from the tip of the cutting tool 1420 to the centre of the fiberscope view 1414 may be known. The method may include calculating a second distance 1416 based on the first distance 1412 and the distance from the tip of the cutting tool 1420 to the centre of the fiberscope view 1414. The second distance 1416 may be the distance from the tip of the cutting tool to the targeted incision spot 1406. The method may include aligning the tip of the cutting tool 1420 with the targeted incision spot 1406. The alignment may be based on the calculated second distance 1416. Alignment may be done manually by the surgeon or operator or automatically a motion control system (including the actuator mechanism).

Figure 15:
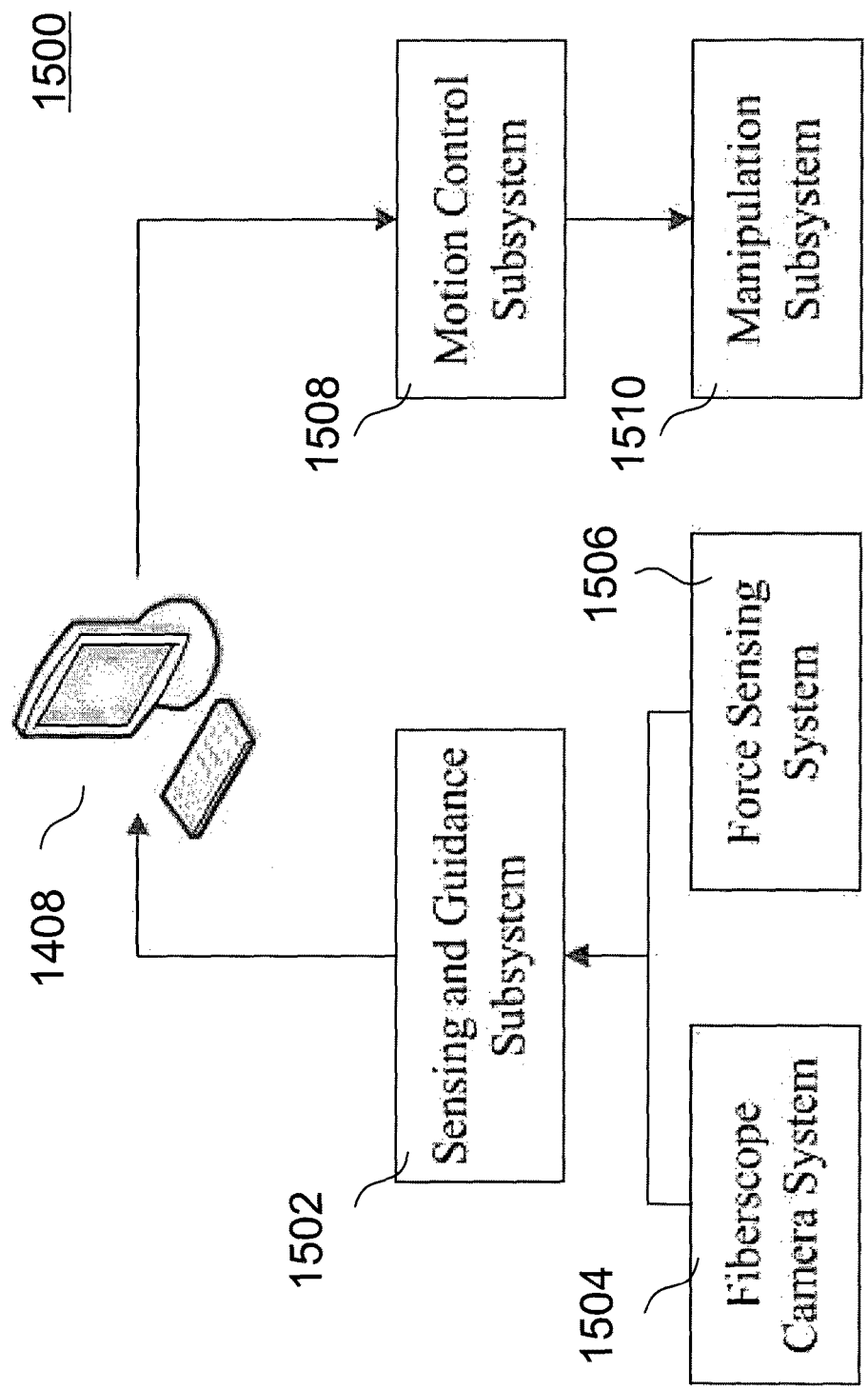
FIG. 15 is a schematic illustrating the sub-systems of the device according to various embodiments.

FIG. 15 is a schematic 1500 illustrating the sub-systems of the device according to various embodiments. The device may include a sensing and guidance sub-system 1502. The sensing and guidance sub-system 1502 may include the fiberscope camera system 1504. The fiberscope camera system 1504 may include the fiberscope or endoscope. The sensing and guidance sub-system 1502 may include the force sensing system 1504. The force sensing system 1504 may include the force sensor. The outputs of the sensing and guidance sub-system may be processed by a processor or a computer 1508. The processor or computer 1508 may control a motion control system 1508. The motion control system 1508 may include the actuator mechanism. The actuator mechanism may include the cutter retraction mechanism. The motion control system 1508 may further include a motion controller coupled to the actuator mechanism. The motion control system 1508 controls the manipulation system 1510. The manipulation system 1510 includes the holder and the cutting tool.

FIG. 16 is a schematic 1600 illustrating a method of using a device to insert an implant into a human or animal body. The method may include, in 1602, operating the device to move an operable portion of the device along a first axis and to move or vibrate the operable portion of the device along a second axis perpendicular to the first axis to make an incision on the human or animal body. The method may further include, in 1604, using the device to insert the implant at least partially through the incision on the human or animal body.

In other words, the method may include moving the operable portion of the device along the first axis and along the second axis to firstly make an incision on a human or animal body and secondly to insert an implant at least partially through the incision.

In various embodiments, a device for use in a method of inserting an implant into a human or animal body may be provided. The method may include operating the device to move an operable portion of the device along a first axis and to move or vibrate the operable portion of the device along a second axis perpendicular to the first axis to make an incision on the human or animal body. The method may further include using the device to insert the implant at least partially through the incision on the human or animal body.

The method may include operating the device to move the operable portion of the device along the first axis and to move or vibrate the operable portion of the device along the second axis to insert the implant at least partially through the incision on the human or animal body.

The operable portion may include an elongated holder having a length extending from a first end of the holder to a second end of the holder. The elongated holder may be configured to hold the implant at the first end of the holder. The operable portion may further include a cutting tool. The cutting tool may be configured to make the incision on the human or animal body. The method may include using a plurality of claws at a first end of the holder to hold or secure the implant. The method may further include using the cutting tool to hold or secure the implant. The cutting tool may include a two-step cutting edge.

The holder may include a cavity extending from the first end of the holder to the second end of the holder, the cavity of the elongated holder configured to receive the cutting tool. The device may include a cutter retraction mechanism configured to move the cutting tool between a first position and a second position. The cutting tool may be received in the cavity of the elongated holder when the cutting tool is in the first position. The cutting tool may be protruded from the cavity of the elongated holder for making the incision on the human or animal body when the cutting tool is in the second position.

Additionally or alternatively, the cutting tool may be configured to move the cutting tool between the first position, the second position and an intermediate position between the first and second position.

The method may include moving the cutting tool between the first and the second position. The method may include moving the cutting tool between the first position, the second position and an intermediate position between the first and second position. Moving the cutting tool may be actuated by a cutter retraction mechanism.

The cutter retraction mechanism may include a servo motor. The cutter retraction mechanism may further include a crank having a first end and a second end. The first end may be coupled to the servo motor. The second end may be coupled to the cutting tool. The crank may configured to convert rotational motion of the servo motor to linear motion of the cutting tool between the first position and the second position. The method may include moving the cutting tool between the first and the second position (or moving the cutting tool between the first position, the second position and an intermediate position between the first and second position) by converting rotational motion of the servo motor to linear motion of the cutting tool between the first position and the second position (or between the first position, the second position and the intermediate position).

The cutting tool may include a hollow channel.

The operable portion may further include a fiberscope or an endoscope arranged at least partially within the hollow channel of the cutting tool. It may also be envisioned that instead of a fiberscope or endoscope, the operable portion may include any other optical element or optical mechanism for capturing an image. The method may include capturing the image of the human or animal body using the fiberscope or endoscope or optical element/mechanism. The method may also include identifying or determining a targeted incision spot for making the incision from the image. The method may further include aligning the tip of the cutting tool to the targeted incision spot either manually or automatically.

The actuator mechanism may include an actuator to move the operable portion along the first axis. The actuator mechanism may also include a further actuator to move the operable portion along the second axis.

Moving the operable portion along the first axis and moving (or vibrating) the operable portion along the second axis may be carried out simultaneously or sequentially.

In various embodiments, the device may include a movable portion and a fixed portion. The operable portion may be mounted on the movable portion. The device may include a force sensor coupled between the fixed portion and the movable portion, the force sensor configured to detect the force applied to the movable portion. The method may include detecting or measuring the force exerted on the operable portion by detecting or measuring the force on the movable portion. The movable portion and the operable portion may be considered as one rigid body.

In various embodiments, the device may include the implant. The implant may be a grommet. In various embodiments, the method may be partially or fully automated. The moving of the operable portion of the device along the first axis and the moving of the operable portion of the device along the second axis to make an incision on the human or animal body may be controlled by a computer algorithm or software. Using the device to insert the implant at least partially through the incision on the human or animal body may be controlled by a computer algorithm or software.

Various embodiments may allow for efficient operation without need for general anesthesia. The patient may be awake during the surgical procedure. The device may be fast acting, precise and yield intelligently controlled motion sequences which minimizes trauma on the patient. Various embodiments may improve the success of the procedure.

Various embodiments may reduce the dependence of the surgeon or operator's skills. The human effort may be reduced mainly to the initial part of guiding and positioning the device relative to the body part such as the ear drum membrane. The incision and implant insertion may be accomplished automatically by the device.

Various embodiments may lead to reduced costs and delay. As the need for an experienced surgeon and/or a surgical room with support is reduced, the procedure may be efficiently administered leading to reduced costs and delay.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A device for inserting an implant on a human or animal body, the device comprising:
   an operable portion configured to make an incision on the human or animal body and configured to hold the implant for insertion on the human or animal body, the operable portion comprising a cutting tool; and
   an actuator mechanism coupled to the operable portion, the actuator mechanism comprises a motor drive configured to move the operable portion along a first axis and further comprises a further motor drive configured to vibrate the operable portion along a second axis substantially perpendicular to the first axis so that the incision is made by the cutting tool;
   wherein the further motor drive is configured to move the operable portion along the second axis in a first direction;
   wherein the motor drive is configured to move the operable portion along the first axis sequentially after the operable portion is moved along the second axis in the first direction; and
   wherein the further motor drive is further configured to move the operable portion along the second axis in a second direction opposite the first direction sequentially after the operable portion is moved along the first axis so as to insert a portion of the implant in the incision on the human or animal body after the incision is made before fully inserting the implant through the incision.

2. The device according to claim 1, wherein the operable portion comprises:
   an elongated holder having a length extending from a first end of the holder to a second end of the holder, the elongated holder configured to hold the implant at the first end of the holder.

3. The device according to claim 2, wherein the elongated holder further comprises a plurality of claws to hold the implant at the first end of the holder.

4. The device according to claim 2, wherein the elongated holder comprises a cavity extending from the first end of the holder to the second end of the holder, the cavity of the elongated holder configured to receive the cutting tool.

5. The device according to claim 4, wherein the actuator mechanism further comprises:

a cutter retraction mechanism configured to move the cutting tool between a first position and a second position;

wherein the cutting tool is received in the cavity of the elongated holder when the cutting tool is in the first position; and wherein the cutting tool is protruded from the cavity of the elongated holder for making the incision on the human or animal body when the cutting tool is in the second position.

6. The device according to claim 5, wherein the cutter retraction mechanism comprises:

a servo motor;

a crank having a first end and a second end, the first end coupled to the servo motor, the second end coupled to the cutting tool;

wherein the crank is configured to convert rotational motion of the servo motor to linear motion of the cutting tool between the first position and the second position.

7. The device according to claim 1, wherein the cutting tool comprises a hollow channel; and wherein the operable portion further comprises a fiberscope arranged at least partially within the hollow channel of the cutting tool.

8. The device according to claim 1, wherein the device comprises a movable portion and a fixed portion;

wherein the operable portion is mounted on the movable portion;

and wherein the device further comprises:

a force sensor coupled between the fixed portion and the movable portion, the force sensor configured to detect the force applied to the movable portion.

9. The device according to claim 1, the device further comprising the implant.

10. The device according to claim 9, wherein the implant is a grommet.

11. A method of using a device to insert an implant into a human or animal body, the device comprising:

an operable portion configured to make an incision on the human or animal body and configured to hold the implant for insertion on the human or animal body; and an actuator mechanism coupled to the operable portion, the actuator mechanism configured to move the operable portion along a first axis and configured to move the operable portion along a second axis substantially perpendicular to the first axis;

wherein the operable portion comprises a cutting tool;

wherein the actuator mechanism comprises a motor drive and a further motor drive; and wherein the method comprises:

operating the device in such a manner that the motor drive moves the operable portion of the device along the first axis and the further motor drive vibrates the operable portion of the device along a second axis perpendicular to the first axis so that the cutting tool makes the incision on the human or animal body;

operating the device in such a manner that the further motor drive moves the operable portion along the second axis in a first direction, the motor drive moves the operable portion along the first axis sequentially after the operable portion is moved along the second axis in the first direction, and the further motor drive moves the operable portion along the second axis in a second direction opposite the first direction sequentially after the operable portion is moved along the first axis so as to insert a portion of the implant in the incision on the human or animal body after the incision is made before fully inserting the implant through the incision.

12. The method according to claim 11, wherein the incision is made on an ear membrane.

13. The method according to claim 12, wherein the implant is inserted at least partially through the incision on the ear membrane.

14. The method according to claim 11, wherein the implant is a grommet.

* * * * *